US00PP33561P2

(12) United States Plant Patent
Mehlenbacher et al.

(10) Patent No.: US PP33,561 P2
(45) Date of Patent: Oct. 19, 2021

(54) ***CORYLUS* PLANT NAMED 'OSU 541.147'**

(50) Latin Name: ***(Corylus americana* x *Corylus avellana)* x *Corylus avellana* cultivar**
Varietal Denomination: OSU 541.147

(71) Applicants: Oregon State University, Corvallis, OR (US); Rutgers, The State University of New Jersey, New Brunswick, NJ (US); Board of Regents of the University of Nebraska, Lincoln, NE (US); Arbor Day Foundation, Lincoln, NE (US)

(72) Inventors: Shawn A. Mehlenbacher, Corvallis, OR (US); David C. Smith, Corvallis, OR (US)

(73) Assignees: Oregon State University, Corvallis, OR (US); Rutgers, the State University of New Jersey, New Brunswick, NJ (US); Board of Regents of the University of Nebraska, Lincoln, NE (US); Arbor Day Foundation, Lincoln, NE (US)

( * ) Notice: Subject to any disclaimer, the term of this patent is extended or adjusted under 35 U.S.C. 154(b) by 0 days.

(21) Appl. No.: 17/006,407

(22) Filed: Aug. 28, 2020

(51) Int. Cl.
*A01H 5/08* (2018.01)
*A01H 6/00* (2018.01)

(52) U.S. Cl.
USPC ..... Plt./152

(58) Field of Classification Search
USPC ..... Plt./216, 152
See application file for complete search history.

(56) References Cited

PUBLICATIONS

Molnar et al. 2010. Survey of *Corylus* Resistance to Anisogramma anomala from different geographic locations. HortScience 45(5) 832-836. (Year: 2010).*
Molnar, Thomas J., "Genetic Resistance to Eastern Filbert Blight in Hazelnut (*Corylus*)," Dissertation, New Brunswick, NJ, Rutgers, The State University of New Jersey, 2006 (121 pages).

* cited by examiner

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct interspecific hybrid *Corylus* plant named 'OSU 541.147' characterized by a vigorous, upright growth habit, the production of nuts with round kernels that fall free of the husk at maturity, and resistance to eastern filbert blight caused by the fungus *Anisogramma anomala* (Peck) E. Müller.

8 Drawing Sheets

Specification includes a Sequence Listing.

ACKNOWLEDGMENT OF GOVERNMENT SUPPORT

This invention was made with government support under 2016-51181-25412 awarded by USDA-National Institute of Food and Agriculture, under 58-5358-4-025 awarded by USDA-Agricultural Research Service, and under 18-13-202 awarded by USDA-Agricultural Marketing Service. The government has certain rights in the invention.

Botanical denomination: (*Corylus americana* x *Corylus avellana*) x *Corylus avellana* cultivar.

Variety designation: 'OSU 541.147'.

PARTIES TO JOINT RESEARCH AGREEMENT

Oregon State University, Rutgers, the State University of New Jersey, Board of Regents of the University of Nebraska, and Arbor Day Foundation executed a Joint Research Agreement on or before the date subject matter disclosed and claimed by the present application was made, and such subject matter was made as a result of activities undertaken within the scope of the Joint Research Agreement.

BACKGROUND

The present invention relates to a new and distinct cultivar of hybrid *Corylus* plant, botanically known as (*Corylus americana* x *Corylus avellana*) x *Corylus avellana*, and hereinafter referred to by the name 'OSU 541.147'.

The new *Corylus* plant resulted from a controlled cross of the female parent 'NY 616' (*Corylus americana* 'Rush' x *Corylus avellana* 'Barcelona') (unpatented) x male parent *Corylus avellana* 'OSU 226.118' (unpatented) made in February 1990 (FIG. 1). Hybrid seeds resulting from the cross were harvested in August 1990. They were provided a period of moist chilling, subsequently germinated, and the seedlings were grown in the greenhouse during the summer of 1991. From this cross, a total of 125 seedling trees were planted in a research field in Corvallis, Oreg., in October 1991. 'OSU 541.147' was discovered and selected as a single plant within that progeny of the stated cross-pollination. It was originally assigned the designation 'OSU 541.147', which indicates the row and tree location of the original seedling.

The female parent is a tree labeled 'NY 616' in row M and tree 1 (M01) in the variety plot in Corvallis, Oreg. It is an unpatented $F_1$ *Corylus americana* x *Corylus avellana* selection developed in New York from a cross of *Corylus americana* 'Rush' x *C. avellana* 'Barcelona' (Slate, 1930). 'Rush' is a *Corylus americana* selection from southeastern Pennsylvania. 'Barcelona' is an old *Corylus avellana* cultivar from Spain that is widely distributed in Europe and was introduced in the U.S. in about 1885 (Mehlenbacher and Miller, 1989). 'Barcelona' is more than 200 years old and is known under several different names, including 'Castanyera' in Tarragona (Spain), 'Grande' in Asturias (Spain), 'Grada de Viseu' in Portugal, and 'Fertile de Coutard' in France. The female parent contributed incompatibility allele $S_{23}$ to 'OSU 541.147' (Table 1). 'Rush' carries a dominant allele for eastern filbert blight resistance on linkage group 7 (Bhattarai et al., 2017; Coyne et al., 1998).

TABLE 1

Incompatibility alleles of the NY hybrid hazelnuts developed in Geneva, New York, and the *Corylus avellana* parents. Also shown are the field locations at the USDA National Clonal Germplasm Repository. 'NY 616', the parent of 'OSU 541.147', carried $S_{23}$.

| Selection | S-alleles | Location | Listed Parentage |
|---|---|---|---|
| 'Buchanan' (unpatented) | 12 15 | N02.53 | 'Rush' × 'Barcelona' |
| 'Reed' (unpatented) | 12 15 | N14.13 | 'Rush' × 'Hall's Giant' |
| 'Potomac' (unpatented) | 5 12 | N01.53 | 'Rush' × 'DuChilly' |
| 'NY 104' (unpatented) | 14 23 | N05.42 | 'Rush' × 'DuChilly' |
| 'NY 110' (unpatented) | 10 12 | N02.42 | 'Rush' × 'DuChilly' |
| 'NY 200' (unpatented) | 15 23 | N02.44 | 'Rush' × 'Hall's Giant' |
| 'NY 398' (unpatented) | 15 23 | N04.22 | 'Rush' × 'Red Lambert' |
| 'NY 485' (unpatented) | 12 14 | N03.28 | 'Rush' × 'DuChilly' |
| 'NY 529' (unpatented) | 3 12 | N04.28 | 'Rush' × 'Daviana' |
| 'NY 588' (unpatented) | 15 23 | N01.30 | 'Rush' × 'Red Lambert' |
| 'NY 616' (unpatented) | 1 23 | N04.47 | 'Rush' × 'Barcelona' |
| 'NY 1329' (unpatented) | 3 23 | N03.24 | 'Rush' × 'Cosford' |
| 'NY 1408' (unpatented) | 11 23 | N02.24 | 'Rush' × 'Cosford' |
| 'NY 1464' (unpatented) | 11 23 | N01.28 | 'Rush' × 'Cosford' |
| 'NYF-20' (unpatented) | 14 25 | N02.22 | 'NY 157' o.p. |
| 'NYF-45' (unpatented) | 12 ? | N05.47 | 'Snyder' × 'NY 485' |
| 'Barcelona' (unpatented) | 1 2 | | possibly was 'Gustav's Zeller' |
| 'Cosford' (unpatented) | 3 11 | | |
| 'DuChilly' (unpatented) | 10 14 | | syn. 'Italian Red' |
| 'Hall's Giant' (unpatented) | 5 15 | | |
| 'Red Lambert' (unpatented) | unknown | | |
| 'White Lambert' (unpatented) | 5 10 | | |
| 'Gustav's Zeller' (unpatented) | 15 20 | | |
| 'Rush' (unpatented) | 12 23 | | by exam of progeny |

The male parent 'OSU 226.118' is an unreleased selection.

'OSU 541.147' was asexually reproduced by rooted suckers in 1997 through 2006 in Corvallis, Oreg. The unique features of this new *Corylus* are stable and reproduced true-to-type in successive generations of asexual reproduction.

SUMMARY

The following traits have been observed and are determined to be the unique characteristics of 'OSU 541.147'. These characteristics in combination distinguish 'OSU 541.147' as a distinct cultivar:

1. Vigorous and upright plant habit.
2. Green to dark-green color of developing and fully expanded leaves during the spring and summer.
3. High level of resistance to eastern filbert blight (EFB) caused by the fungus *Anisogramma anomala* (Peck) E. Müller. The source of this resistance is from *C. americana* 'Rush' (unpatented; Bhattarai, et al., 2017), which differs from the single dominant allele conferred from 'Gasaway' (unpatented, Mehlenbacher et al., 1991), which protects *Corylus avellana* 'McDonald' (U.S. Plant Pat. No. 28,200, Mehlenbacher et al., 2016), 'Wepster' (U.S. Plant Pat. No. 27,141, Mehlenbacher et al., 2014), 'Dorris' (U.S. Plant Pat. No. 25,022, Mehlenbacher et al., 2014), 'Jefferson' (unpatented, Mehlenbacher et al., 2011a), 'Yamhill' (unpatented, Mehlenbacher et al., 2009), and several other *Corylus avellana* cultivars and pollenizers.
4. Expression of incompatibility alleles $S_8$ and $S_{23}$ in the styles.

Comparisons in several replicated plantings in Corvallis, Oreg., Cream Ridge, N.J., and East Brunswick, N.J., show that plants of 'OSU 541.147' differed from plants of the *Corylus avellana* cultivars 'Barcelona' (unpatented), 'Tonda di Giffoni' (unpatented), 'Yamhill', 'Jefferson', 'McDonald', 'Wepster' and other cultivars and selections of *Corylus avellana* known to the Inventors, primarily in their response to EFB present in New Jersey, a region where the pathogen is native and highly genetically diverse (Muehlbauer et al., 2019). They also differed in S-alleles, nut size, kernel percentage (ratio of kernel weight to nut weight), frequency of defects (blank nuts, moldy kernels, twin kernels, etc.), time of pollen shed, and length of the husk or involucre. For example:

Eastern filbert blight response in New Jersey: In a multi-year trial in East Brunswick, N.J., 'OSU 541.147' showed no eastern filbert blight compared to the proportion of EFB-diseased wood across the canopy calculated to be 20.4% for 'Yamhill', 31.2% for 'Jefferson', 48.6% for 'Gasaway', and 67.0% for 'Barcelona'.

Pollen shed: 'OSU 541.147' generally sheds pollen in East Brunswick, N.J., a week after 'Ratoli' (unpatented, minor cultivar from Tarragona, Spain), 2-3 days after 'Yamhill' and 'Santiam' (unpatented, Mehlenbacher et al., 2007), and 2-3 days prior to 'Jefferson' and 'Gasaway'. In Corvallis, Oreg., OSU 541.147 sheds pollen between 'McDonald' (U.S. Plant Pat. No. 28,200) and 'PollyO' (U.S. Plant Pat. No. 32,459). 'OSU 541.147'=descriptor-5.

Husk Length: 'OSU 541.147' is 1.6 times nut length, slightly shorter than 'Barcelona', while 'Wepster' is 2.0 times nut length. Husks have glandular trichomes.

'OSU 541.147' produces small kernels that are suitable for the blanched kernel market for use in confections and baked goods. 'OSU 541.147' combines resistance to eastern filbert blight (evaluated against *Anisogramma anomala* present in New Jersey, Oregon, Michigan, New York, Pennsylvania, Massachusetts, Wisconsin, and Minnesota [Molnar et al., 2010a]) with round nuts and kernels and moderately good kernel blanching. The tree is vigorous with an upright habit that produces a desirable orchard tree when pruned to a single stem.

Field observations in Corvallis, Oreg., Cream Ridge, N.J., and East Brunswick, N.J., and results from greenhouse-based inoculations performed in New Brunswick, N.J., indicate that 'OSU 541.147' expresses resistance to EFB caused by the fungus *Anisogramma anomala*. The resistance is conferred by the single dominant allele from *Corylus americana* 'Rush', found on hazelnut linkage group 7 (Bhattarai et al., 2017), which is unlike the cultivars currently grown in Oregon protected by the single dominant 'Gasaway' resistance allele found on linkage group 6 (Mehlenbacher et al., 2006). EFB is now present throughout the Willamette Valley of Oregon where 99% of the U.S. hazelnut crop is grown and is endemic to the eastern U.S. and southern Canada, where it has severely limited commercial production of European hazelnut. Fungicide applications and pruning to remove cankers are currently used to manage the disease in orchards of 'Barcelona' and other susceptible cultivars in the Pacific Northwestern U.S. 'OSU 541.147' was selected in the Willamette Valley of Oregon and subsequently evaluated in New Jersey and is adapted to the climate in both regions. 'OSU 541.147' is suitable for planting in areas with high EFB disease pressure. It has shown resistance in the eastern U.S. where the EFB fungus is native and genetically diverse (Muehlbauer et al., 2019).

The foregoing and other objects and features of the disclosure will become more apparent from the following detailed description, which proceeds with reference to the accompanying figures.

BRIEF DESCRIPTION OF THE DRAWINGS

The accompanying color photographs illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

FIG. 6 shows the time of female receptivity (bottom, red), pollen shed (top, green), and vegetative budbreak of 'OSU 541.147' and other hazelnut cultivars in Corvallis, Oreg. (December 2018-March 2019).

FIG. 7 shows the time of female receptivity (bottom, red), pollen shed (top, green), and vegetative budbreak of 'OSU 541.147' and other hazelnut cultivars in East Brunswick, N.J. (December 2017 to March 2018).

FIG. 8 shows the time of female receptivity (bottom, red), pollen shed (top, green), and vegetative budbreak of 'OSU 541.147' and other hazelnut cultivars in East Brunswick, N.J. (December 2018 to March 2019).

SEQUENCE LISTING

Figure 1:
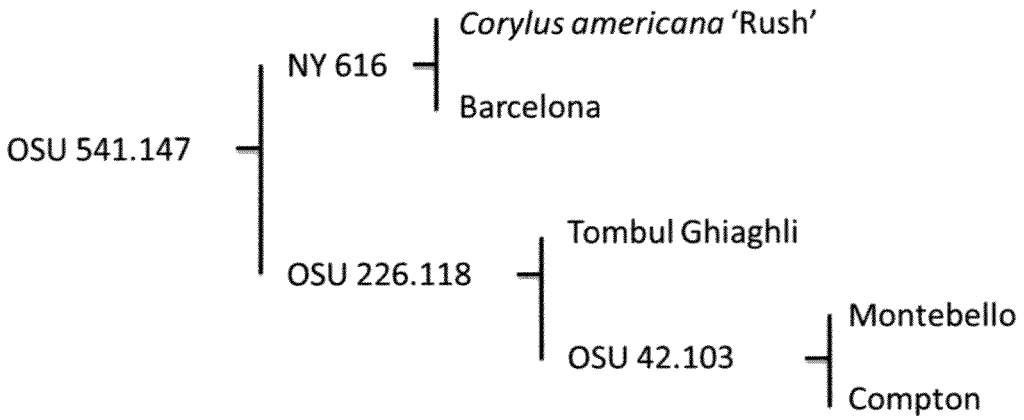
FIG. 1 shows the pedigree of new cultivar 'OSU 541.147'.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NOS: 1-40 are primer sequences that can be used for genetic fingerprinting.

DETAILED DESCRIPTION

The cultivar 'OSU 541.147' has not been observed under all possible environmental conditions. The phenotype may vary somewhat with variations in environment such as temperature and light intensity, without, however, any variance in genotype. The aforementioned photographs and following observations and measurements describe plants grown in East Brunswick, N.J., under commercial practice outdoors in the field during the spring and summer. The plant used for the photographs and description were from a seven-year-old tree propagated by tie-off layerage and growing on its own roots. In the following description, color references are made to The Royal Horticultural Society Colour Chart, 1966 Edition, except where otherwise noted and where general terms of ordinary dictionary significance are used. The list of UPOV descriptors are from the Mar. 28, 1979 Hazelnut guidelines from UPOV.

Botanical classification: *Corylus* cultivar 'OSU 541.147'.

Parentage: Female, or seed, parent is 'NY 616' (*Corylus americana* x *Corylus avellana*). It was selected from a cross of *Corylus americana* 'Rush' x *Corylus avellana* 'Barcelona' (Slate, 1930). 'Rush' is a *Corylus americana* selection from southeastern Pennsylvania. 'Barcelona' is an old *Corylus avellana* cultivar from Spain that is widely distributed in Europe and was introduced in the U.S. in about 1885 (Mehlenbacher and Miller, 1989). 'Barcelona' is more than 200 years old and is known under several different names, including 'Castanyera' in Tarragona (Spain), 'Grande' in Asturias (Spain), 'Grada de Viseu' in Portugal, and 'Fertile de Coutard' in France. 'Rush' has been shown to transmit a dominant allele for resistance to EFB, which has been mapped to a different linkage group than the allele from 'Gasaway'. The 'Rush' allele that protects 'OSU 541.147' has been shown to provide resistance in the presence of multiple populations of the EFB fungus *Anisogramma anomala* (Molnar et al., 2010a, 2019; Bhattarai et al., 2017). Male, or pollen, parent is *Corylus avellana* 'OSU 226.118' (unpatented breeding selection). 'OSU 226.118' is the result of the cross of 'Tombul Ghiaghli' (unpatented, Greek origin) x OSU 42.103 (unpatented). 'OSU 42.103' is the result of a cross of 'Montebello' (unpatented) x 'Compton' (unpatented).

Incompatibility alleles: 'OSU 541.147' has incompatibility alleles $S_8$ and $S_{23}$. Hazelnuts are a wind-pollinated, monoecious species that exhibit a sporophytic self-incompatibility system controlled by a single locus designated as the S-locus with 33 alleles (Mehlenbacher, 2014). To develop 'OSU 541.147', branches of 'NY 616' were emasculated and covered to prevent foreign pollen contamination. Controlled pollinations used a mixture of pollens of three breeding selections whose S-alleles were known: 'OSU 55.129' ($S_2$, $S_4$), 'OSU 167.002' ($S_3$, $S_{10}$) and 'OSU 226.118' ($S_1$, $S_8$). Fluorescence microscopy identified the male parent of 'OSU 541.147' ($S_8$, $S_{23}$) as 'OSU 226.118' because of the common allele $S_8$. For comparison, *Corylus avellana* 'Sacajawea' has the alleles $S_1$ and $S_{22}$. 'Tonda di Giffoni' has the alleles $S_2$ and $S_{23}$, 'Tonda Pacifica' (U.S. Plant Pat. No. 22,715, Mehlenbacher et al., 2011b) and 'Wepster' have alleles $S_1$ and $S_2$, and 'McDonald' has alleles $S_2$ and $S_{15}$. *Corylus americana* 'Rush' has alleles $S_{12}$ and $S_{23}$.

Propagation (type rooted suckers):

*Time to initiate roots*.—About 30 days at 20° C.

*Time to produce a rooted young plant*.—About six months at 22° C.

*Root description*.—Fine to thick; freely branching; creamy white in color.

Propagation (type whip grafting):

*Time to budbreak on the scions*.—About 14 days at 25° C.

*Time to produce a grafted plant*.—About six months at 25° C.

Figure 2:
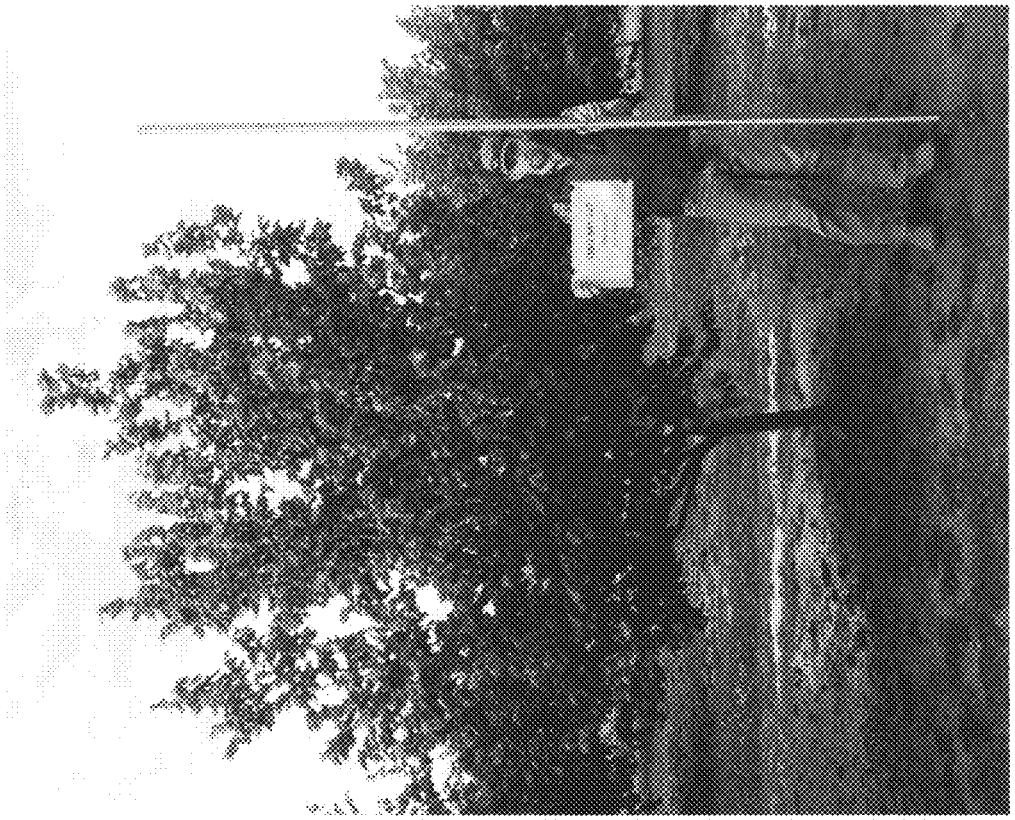
FIG. 2 shows a tree of the new cultivar 'OSU 541.147' hazelnut in July of the seventh leaf pruned to a single trunk.

Plant description (descriptions are from plants grown in New Jersey unless otherwise noted):

*General appearance*.—Natural habit is perennial shrub, but in commercial orchards, is a single trunk tree. Upright plant habit. See FIG. 2.

*Growth and branching habit*.—Freely branching; about 15 lateral branches develop per plant. Pinching, that is, removal of the terminal apices, enhances branching with lateral branches potentially forming at every node.

*Vigor*.—Vigorous, upright growth habit.

*Size*.—Plant height is about 3.6 meters; plants grown in Oregon: plant diameter or spread is about 3.2 meters (in July, seventh leaf).

*Trunk at* 30 *cm above the soil line*.—In a trial planted in Corvallis, Oreg. in 2014, trunk diameter was 7.90 cm and cross-sectional area was 49 $cm^2$ in December, 2019. This is slightly smaller than 'Jefferson' in the same trial.

*Trunk color*.—197B.

Lateral branch description:

*Length*.—About 20.4 cm. Ranges from 14.0 cm to 26.0 cm.

*Diameter*.—About 4.3 mm. Ranges from 3.0 mm to 5.0 mm.

*Internode length* (*at base*).—About 0.75 cm.

*Internode length* (*at tip*).—About 3.6 cm. Ranges from 2.5 cm to 5.0 cm.

*Texture*.—Smooth, pubescent.

*Strength*.—Strong.

*Color, immature*.—143C.

*Color, mature*.—146B.

*Color of previous seasons branches*.—199C.

Foliage description:

*Arrangement*.—Alternate, simple.

*Length*.—About 9.6 cm. Ranges from 7.5 cm to 11.5 cm.

*Width*.—About 7.1 cm. Ranges from 6.0 cm to 9.0 cm.

*Shape*.—Oblong to ovate.

*Apex*.—Obtuse to acute.

*Base*.—Cordate.

*Margin*.—Serrate.

*Texture, upper and lower surfaces*.—Slightly pubescent.

*Venation pattern*.—Pinnate.

*Color*.—Developing foliage — upper surface 144A, lower surfaces, 144B. Fully expanded foliage — upper surface: spring and summer, 137B; late summer and fall, 137B. Fully expanded foliage, lower surface: spring and summer, 137D; late summer and fall, 137D. Venation, upper surface: spring and summer, 145A; late summer and fall, 145A.

*Venation, lower surface*.—Spring and summer, 145A; late summer and fall, 145A.

Leaf bud description:

*Shape*.—Globular.

*Time of leaf budbreak*.—Medium, Descriptor-5. 'OSU 541.147' budbreak is about 8 days before 'Jefferson', four days after 'Yamhill', and concurrent with 'Santiam'.

*Color of leaf buds*.—145B.

*Leaf bud shape* (*winter*).—Ovoid, Descriptor-2.

*Leaf bud color* (*winter*).—Reddish green, Descriptor-2.

Petiole description:

*Length*.—About 9.3 mm. Ranges from 8.0 cm to 15.0 mm.

*Diameter*.—About 1.8 mm. Ranges from 1.0 mm to 2.0 mm.

*Texture, upper and lower surfaces*.—Pubescent.

*Color of petiole*.—143C.

Flower description:

*Male inflorescences*.—Catkins

*Color prior to elongation*.—176D.

*Catkin length*.—31.7 mm.

*Female inflorescence style color*.—047B.

*Time of female flowering*.—Medium (January 20 to February 10), Descriptor-5.

*Time of female flowering compared to male flowering*.—Protogyny, Descriptor-1.

*Involucre constriction*.—The involucre is not constricted, Descriptor-1.

*Involucre length*.—1.6 times length of nut, Descriptor-7.

*Size of husk indentation*.—Medium, Descriptor-7 (similar to 'Negret'), about 50% of husk length.

*Strength of serration of indentation*.—Medium, Descriptor-5.

*Thickness of callus at base*.—Thick, Descriptor-7, (similar to 'Barcelona') or about 2 mm.

*Pubescence on husk*.—Present, Descriptor-9.

*Density of hairiness of involucre*.—Strong, Descriptor-7.

*Jointing of bracts*.—On one side, Descriptor-2.

Nut description:

*Length*.—*Average* 17.4 mm.

*Width*.—*Average* 17.5 mm.

*Depth*.—*Average* 14.7 mm.

*Nut shape*.—Globular, Descriptor-2. See FIG. 5.

*Nut shape index*.—(Width+Depth)/2*Length=0.92.

*Nut compression index*.—(Width/Depth)=1.19.

*Nut weight*.—2.62 g (in Corvallis, Oreg.).

*Kernel weight*.—1.16 g (in Corvallis, Oreg.).

*Kernel percentage* (*kernel weight/nut weight*).—44.1% (in Corvallis, Oreg.).

Figure 3:
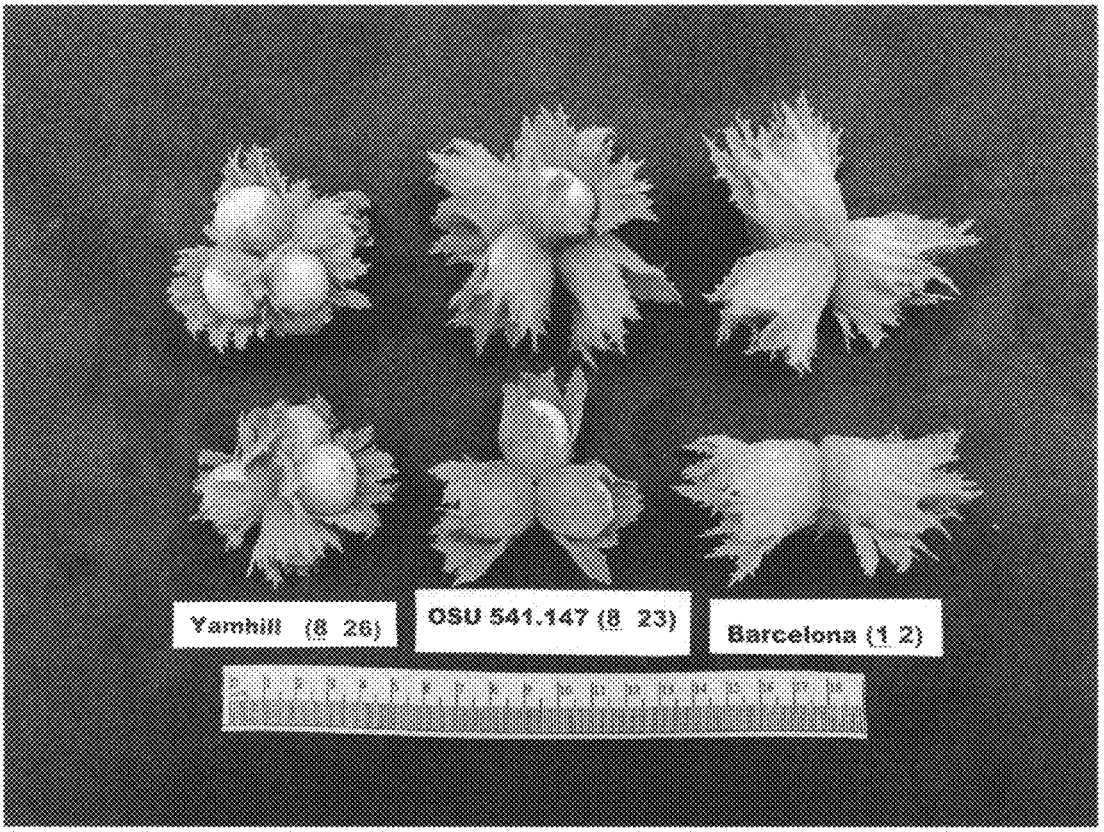
FIG. 3 shows immature nuts and husks of 'Yamhill', 'OSU 541.147' and 'Barcelona' in July of the seventh leaf.

*Number of fruits per cluster*.—Three to four. See FIGS. 3 and 4.

*Nutshell coloration*.—165A.

*Number of stripes on shell*.—Medium (about 20), Descriptor-5.

*Shape of fruit apex*.—Flat, Descriptor-1.

*Prominence of fruit apex*.—Slightly prominent, Descriptor-3.

*Size of fruit pistil scar on shell*.—Medium, Descriptor-5.

*Hairiness of top of fruit*.—Medium, Descriptor-5.

*Curvature of nut basal scar*.—Flat, Descriptor-3 (small) and similar to 'Negret'. The raised part of the shell has dimensions 3.3×1.4 mm.

*Size of basal scar*.—Descriptor-5. Average measurements 14.3×13.4 mm.

*Double kernels*.—Absent.

*Kernel shape*.—Globular, Descriptor-2.

*Shape of kernel in cross-section*.—Circular, Descriptor-2.

*Lateral groove in kernel*.—Present.

*Corkiness of pellicle of kernel*.—Slightly corky, Descriptor-3.

*Color of the fiber on the kernel*.—165A (Royal Horticultural Society Colour Chart Fifth Edition, 2007).

*Color of the pellicle under the fiber*.—165B (Royal Horticultural Society Colour Chart Fifth Edition, 2007).

Disease/pest resistance: Plants of 'OSU 541.147' are resistant to EFB caused by the fungus *Anisogramma anomala* (Peck) E. Müller. Plants have not been challenged against all populations of *Anisogramma anomala* present in North America (Muehlbauer et al., 2019); however, 'OSU 541.147' has been challenged in field trials and/or greenhouse inoculations with populations from Oregon, New Jersey, Minnesota, Michigan, Massachusetts, New York, and Pennsylvania, and no signs or symptoms of EFB have been observed (Capik and Molnar, 2012; Molnar et al., 2010a). Resistance is derived from its grandparent 'Rush'. 'OSU 541.147' has been trialed in New Jersey since 2002 under high disease pressure with no signs or symptoms of EFB observed (Capik and Molnar, 2012; Molnar et al., 2010a, 2019). In Oregon, all trees of 'OSU 541.147' have remained free of EFB. Fungicide applications are not expected to be needed to control EFB. Susceptibility to bacterial blight caused by *Xanthomonas arboricola* pv. *corylina* has not been quantified, but no trees in the trials in Oregon and New Jersey were affected. Susceptibility to bud mite (*Phytoptus avellanae* Nal.) was rated in trials in Corvallis, Oreg., in mid-December on a scale of 1 (no blasted buds) to 5 (many blasted buds). The average rating for 'OSU 541.147' was 3.5, indicating moderate susceptibility comparable to 'Clark' and 'Gamma' (Table 2). With this rating, chemical control of mites will occasionally be needed. Buds blasted by bud mites have not been observed on 'OSU 541.147' in New Jersey.

TABLE 2

Performance of 17 genotypes in a replicated trial planted in Corvallis in Spring, 2014. Four trees per selection in a randomized complete block design.

| Sel | | Yield (kg/tree) | | | |
|---|---|---|---|---|---|
| No | Selection | 2017 | 2018 | 2019 | Total |
| 1 | 'OSU 541.147' | 0.37 | 2.87 | 4.58 | 8.00 |
| 2 | '1250.057' | 1.58 | 2.70 | 3.70 | 7.98 |
| 3 | '1252.068' | 0.75 | 3.46 | 3.93 | 8.15 |
| 4 | '1253.064' | 0.77 | 2.40 | 2.24 | 5.41 |
| 5 | '1292.065' | 1.33 | 2.99 | 4.83 | 9.14 |
| 6 | '1300.073' | 1.96 | 3.33 | 4.51 | 9.80 |
| 7 | '1304.039' | 1.78 | 2.94 | 3.62 | 8.35 |
| 8 | '1307.003' | 1.23 | 3.30 | 5.06 | 9.58 |
| 9 | '1307.055' | 1.35 | 3.93 | 4.06 | 9.34 |
| 10 | '1308.087' | 1.15 | 3.70 | 4.81 | 9.65 |
| 11 | '1310.022' | 0.64 | 2.34 | 2.16 | 5.14 |
| 12 | '1339.074' | 1.17 | 3.89 | 4.55 | 9.60 |
| 13 | '1340.018' | 1.25 | 4.94 | 4.53 | 10.71 |
| 14 | '1341.037' | 1.06 | 2.08 | 4.72 | 7.85 |
| 15 | 'Jefferson' | 2.39 | 4.77 | 4.60 | 11.75 |
| 16 | 'McDonald' | 0.78 | 3.90 | 5.86 | 10.53 |
| 17 | 'Wepster' | 2.16 | 4.59 | 5.33 | 12.08 |
| | LSD (0.05) | 0.57 | 0.95 | 1.14 | 1.81 |

TABLE 2-continued

Performance of 17 genotypes in a replicated trial planted in Corvallis in Spring, 2014. Four trees per selection in a randomized complete block design.

| Sel No | Selection | Trunk diameter | Trunk TCA | Yield efficiency | Bud mite rating |
|---|---|---|---|---|---|
| 1 | 'OSU 541.147' | 7.89 | 49.03 | 0.164 | 3.50 |
| 2 | '1250.057' | 8.39 | 55.29 | 0.143 | 1.70 |
| 3 | '1252.068' | 8.42 | 55.74 | 0.146 | 1.80 |
| 4 | '1253.064' | 6.76 | 35.97 | 0.151 | 1.40 |
| 5 | '1292.065' | 7.79 | 47.80 | 0.192 | 3.10 |
| 6 | '1300.073' | 9.24 | 67.11 | 0.146 | 1.00 |
| 7 | '1304.039' | 6.82 | 36.56 | 0.229 | 1.10 |
| 8 | '1307.003' | 8.90 | 62.34 | 0.152 | 1.10 |
| 9 | '1307.055' | 7.71 | 46.73 | 0.200 | 3.10 |
| 10 | '1308.087' | 9.20 | 66.61 | 0.144 | 2.30 |
| 11 | '1310.022' | 7.97 | 49.99 | 0.104 | 1.00 |
| 12 | '1339.074' | 9.04 | 64.61 | 0.149 | 1.10 |
| 13 | '1340.018' | 9.48 | 70.74 | 0.151 | 1.10 |
| 14 | '1341.037' | 11.26 | 99.64 | 0.079 | 2.80 |
| 15 | 'Jefferson' | 8.19 | 52.90 | 0.222 | 1.30 |
| 16 | 'McDonald' | 9.74 | 60.07 | 0.177 | 2.10 |
| 17 | 'Wepster' | 8.63 | 58.84 | 0.210 | 1.60 |
| | LSD (0.05) | 0.65 | 8.78 | 0.033 | 1.14 |

Yield per tree in each year of evaluation and total of 3 years. There were very few nuts in 2016 and they were not harvested.

Trunk diameter in cm, 30 cm above the soil line, calculated from circumference.

TCA = Trunk cross-sectional area in $cm^2$, calculated from circumference 30 cm above the soil line.

Yield efficiency is the ratio of total yield per tree divided by trunk cross-sectional area (units $kg/cm^2$).

Bud mite susceptibility rated in mid-December on a scale of 1 (no blasted buds) to 5 (many blasted buds).

Temperature tolerance: 'OSU 541.147' was selected in Corvallis, Oreg., and further evaluated in Cream Ridge, N.J. and East Brunswick, N.J., and is targeted for production in USDA Plant Hardiness Zones 6a to 7b. Plants of the new *Corylus avellana* have been observed to tolerate temperatures from −21 to 38° C.

COMPARATIVE DATA

Disease resistance: 'OSU 541.147' differs from existing *Corylus avellana* cultivars based on its source and type of resistance to eastern filbert blight (EFB) caused by *Anisogramma anomala*. Commercial cultivars previously widely grown in Oregon including 'Barcelona' (unpatented), 'Ennis' (unpatented), 'Daviana' (unpatented), 'Butler' (unpatented), etc. are highly susceptible to EFB and cannot be grown in the eastern U.S. without copious applications of chemical fungicides and heavy pruning to remove infected wood. Tree death can occur in the eastern U.S. within five years of exposure to the fungus. The more recently developed cultivars 'Santiam' , 'Yamhill', 'Jefferson', 'Dorris', 'Wepster', and 'McDonald' and their associated pollenizers are protected from EFB by a single resistance gene conferred from *Corylus avellana* 'Gasaway'. This gene provides a high level of resistance in Oregon and Washington where the diversity of the fungus is limited (Muehlbauer et al., 2019), but does not provide a similar level of protection from disease in the eastern U.S. where the pathogen is endemic and genetically diverse (Capik and Molnar, 2012; Molnar et al., 2010b; Muehlbauer et al., 2018). 'OSU 541.147' does not carry the single 'Gasaway' resistance allele. It carries the *Corylus americana* 'Rush' allele, which is a different gene on a different chromosome than 'Gasaway' (Bhattarai, et al., 2017). The allele from 'Rush' has been found to be very effective against the populations of *Anisogramma anomala* present in New Jersey and other locations (Molnar et al., 2010a, 2019).

In a multi-year trial in East Brunswick, N.J., completed in winter 2018 and spanning more than 8 years of exposure to EFB, the average proportion of diseased wood (total length of EFB-diseased stems per tree divided by total length of shoot growth) for 'OSU 541.147' was 0.0% (no EFB) compared to 20.4% for 'Yamhill' (unpatented, Mehlenbacher et al 2009), 31.2% for 'Jefferson' (unpatented, Mehlenbacher et al. 2011a), and 48.6% for 'Gasaway' (unpatented). Previous studies in New Jersey showed the proportion of diseased wood of 'Barcelona' to be 67.0%, 'Tonda di Giffoni' 39%, and 'Sacajawea' 21% (Capik and Molnar, 2012).

Differences were also observed in the number of cankers and average canker length for 'OSU 541.147' in comparison to 'Yamhill', 'Jefferson', and 'Gasaway' in the study completed in 2018. 'OSU 541.147' expressed no cankers. In contrast, 'Gasaway' exhibited an average of 93.0 cankers per tree with an average length of 130.8 cm, 'Jefferson' exhibited an average of 36.9 cankers per tree with an average length of 72.3 cm, and 'Yamhill' exhibited an average of 40.5 cankers per tree with an average length of 37.9 cm. As reported in Capik and Molnar (2012), and as a further point of comparison in regard to EFB response, 'Barcelona' exhibited an average of 20.4 cankers per tree with an average length of 61.9 cm, 'Tonda di Giffoni' exhibited an average of 39.0 cankers per tree with an average length of 24.5 cm, and 'Sacajawea' exhibited an average of 7.7 cankers per tree with an average length of 21.5 cm (Capik and Molnar, 2012).

Nut and kernel characteristics. 'OSU 541.147' hazelnut is targeted for the blanched kernel market and specifically for nut production in the eastern United States in USDA Plant Hardiness Zones 6a to 7b where most existing cultivars of *Corylus avellana* cannot be grown due to the impacts of EFB.

Figure 4:
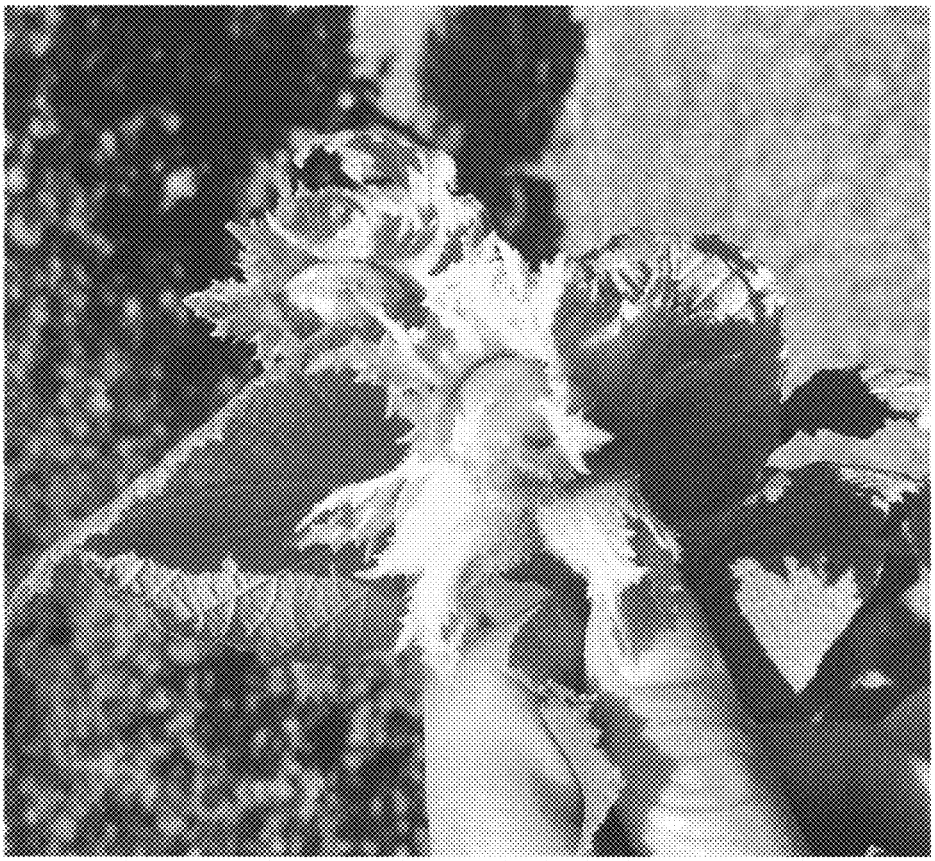
FIG. 4 shows mature nuts and husks of 'OSU 541.147' growing in New Jersey.
Figure 5:
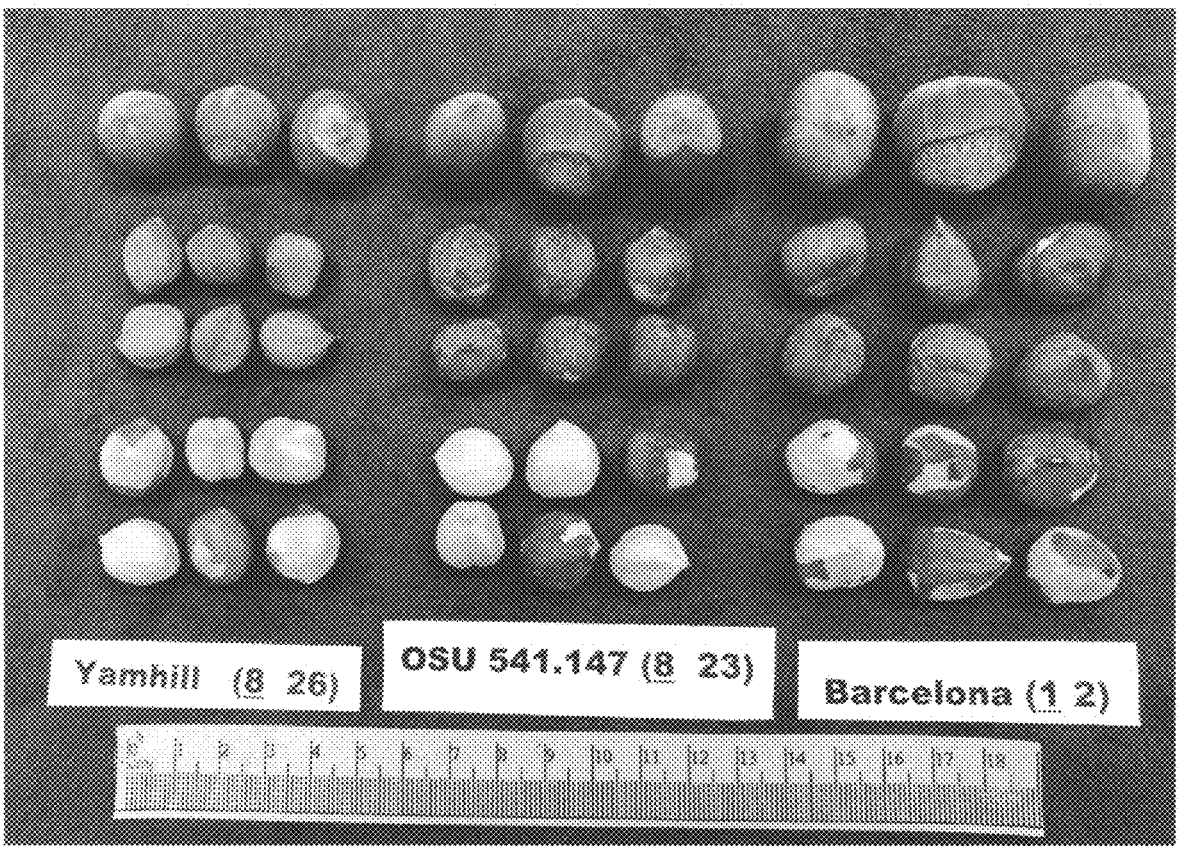
FIG. 5 shows nuts, raw kernels, and blanched kernels of hazelnuts 'Yamhill', 'OSU 541.147' and 'Barcelona'. Top row nuts, rows 2 and 3 raw kernels, rows 4 and 5 blanched kernels.

As shown in FIG. 5, the nut shape is round to somewhat oblong. Kernels are round. The average single nut weight for 'OSU 541.147' over three years (2017-19) is 2.62 g, average single kernel weight is 1.16 g, with an average kernel percentage of 44.1% (FIG. 4, Table 3). Nut weight in the same trial was 3.77 g for 'Jefferson', 2.67 g for 'McDonald' and 2.49 g for 'Wepster'. Kernel weights in the same trial were 1.70 g for 'Jefferson', 1.39 g for 'McDonald' and 1.17 g for 'Wepster'. Kernel percentage in the same trial was 45.2% for 'Jefferson', 52.3% for 'McDonald' and 47.0% for 'Wepster'. 'OSU 541.147' nuts and kernels are significantly smaller than those of 'Barcelona' and 'Jefferson', and intermediate between 'McDonald' and 'Wepster'. In a previous trial (Mehlenbacher et al., 2008), 'Barcelona' had an average nut weight of 3.85 g, average single kernel weight of 1.66 g, and an average kernel percentage of 43.1%.

In the trial planted in 2014 in Corvallis, Oreg., 'Barcelona' had an average single nut weight of 3.77 g, an average single kernel weight of 1.70, and an average kernel percentage of 45.2%. The trees produced a few nuts in 2016, but were not harvested. Nuts were harvested for three years (2017-19), dried, weighed and evaluated. Total nut weight per tree (2017-19) was 8.0 kg for OSU 541.147, which is less than for the checks 'Jefferson', 'McDonald' and 'Wepster' (Table 2). Trunk cross-sectional area (TCA) was 49.03 $cm^2$, or slightly smaller than 'Jefferson'. Yield efficiency, the ratio of total yield to TCA, was a respectable 0.164 $kg/cm^2$ and similar to 'McDonald' (0.177 $kg/cm^2$). Trees have an upright growth habit, and vigor similar to *C. avellana* selections in the *Corvallis* trials.

Raw kernels of 'OSU 541.147' have a medium brown pellicle with a large amount of attached fiber (average rating was 4.0 on a scale of 1 [no fiber] to 4 [much fiber]; Table 3). Pellicle removal after roasting at 150° C. for 15 min and rubbing is rated on a scale of 1 (complete pellicle removal) to 7 (no pellicle removal). Slightly less than half of the pellicle on 'OSU 541.147' kernels is generally removed after roasting with an average rating of 4.5 (Table 3), a value similar to 'Barcelona' (4.2 out of 7.0 as described in Mehlenbacher et al., 2008) and 'Yamhill' (4.1 out of 7.0 as described in Mehlenbacher et al. 2011a). In the trial planted in 2014, pellicle removal after roasting was better for 'McDonald' (3.7 out of 7) and 'Wepster' (3.0 out of 7) (Table 3).

The average percentage of good kernels (kernels free of defects) was calculated for 'OSU 541.147' in the trial planted in 2014 and found to be 85.3% (Table 3). There was on average 9.3% blank nuts, 0.3% moldy kernels, 2.4% nuts with shriveled kernels, and 2.5% poorly filled. The percentage of good kernels for 'OSU 541.147' was considerably higher than that reported for 'Barcelona' in multiple reports from Oregon (60.9% good kernels reported in Mehlenbacher et al. [2008] and 69.4% in Mehlenbacher et al. [2013]). The average percentage of good kernels for 'OSU 541.147' grown in New Jersey is slightly lower than the range reported in Oregon for 'Yamhill', 'Jefferson', 'Dorris', and 'McDonald', however the percentage of moldy nuts was generally higher for these cultivars. The incidence of twin kernels and moldy kernels with black tips is less than 0.1% in both OR and NJ.

TABLE 3

Performance of 17 genotypes in a replicated trial planted in Corvallis in Spring, 2014. Four trees per selection in a randomized complete block design.

| Sel No | Selection | 10-nut weight | 10-kernel weight | Percent kernel | Fiber | Blanching |
|---|---|---|---|---|---|---|
| 1 | 'OSU 541.147' | 26.2 | 11.6 | 44.1 | 4.0 | 4.5 |
| 2 | '1250.057' | 36.9 | 16.4 | 44.5 | 3.4 | 4.2 |
| 3 | '1252.068' | 25.7 | 12.4 | 48.3 | 2.6 | 2.8 |
| 4 | '1253.064' | 28.4 | 13.0 | 45.9 | 1.9 | 3.0 |
| 5 | '1292.065' | 28.2 | 13.1 | 46.6 | 3.5 | 4.3 |
| 6 | '1300.073' | 25.2 | 12.9 | 51.1 | 2.6 | 4.2 |
| 7 | '1304.039' | 27.5 | 12.4 | 45.1 | 2.2 | 3.0 |
| 8 | '1307.003' | 23.7 | 11.9 | 50.2 | 1.0 | 3.0 |
| 9 | '1307.055' | 25.7 | 12.9 | 50.4 | 2.2 | 4.8 |
| 10 | '1308.087' | 30.2 | 13.3 | 44.1 | 2.9 | 4.9 |
| 11 | '1310.022' | 28.8 | 14.0 | 48.7 | 3.5 | 4.9 |
| 12 | '1339.074' | 30.5 | 14.6 | 47.9 | 2.0 | 5.8 |
| 13 | '1340.018' | 27.9 | 13.9 | 49.7 | 3.1 | 3.3 |
| 14 | '1341.037' | 30.4 | 13.5 | 44.3 | 2.3 | 2.1 |
| 15 | 'Jefferson' | 37.7 | 17.0 | 45.2 | 2.8 | 4.1 |
| 16 | 'McDonald' | 26.7 | 13.9 | 52.3 | 2.6 | 3.7 |
| 17 | 'Wepster' | 24.9 | 11.7 | 47.0 | 2.9 | 3.0 |
| | LSD (0.05) | 0.6 | 0.3 | 0.5 | 0.2 | 0.2 |

| Sel | | Frequency (%) | | | | | | | |
|---|---|---|---|---|---|---|---|---|---|
| No | Selection | GD | BL | BS | MO | SF | PF | TW | BT |
| 1 | 'OSU 541.147' | 85.3 | 9.3 | 0.3 | 0.3 | 2.4 | 2.5 | 0.1 | 0.0 |
| 2 | '1250.057' | 85.4 | 4.8 | 0.3 | 2.0 | 1.1 | 6.0 | 0.5 | 0.1 |
| 3 | '1252.068' | 83.7 | 5.9 | 1.5 | 2.1 | 0.8 | 4.3 | 0.5 | 1.6 |
| 4 | '1253.064' | 84.4 | 6.6 | 1.8 | 3.4 | 1.8 | 3.3 | 0.6 | 1.0 |
| 5 | '1292.065' | 83.1 | 9.8 | 0.1 | 1.8 | 0.3 | 4.9 | 0.3 | 0.2 |
| 6 | '1300.073' | 83.6 | 3.5 | 1.8 | 3.5 | 1.6 | 3.9 | 0.2 | 2.3 |
| 7 | '1304.039' | 84.5 | 4.8 | 0.8 | 2.5 | 1.4 | 5.4 | 0.3 | 0.5 |
| 8 | '1307.003' | 86.5 | 7.9 | 0.3 | 2.2 | 1.5 | 2.1 | 0.0 | 0.3 |
| 9 | '1307.055' | 73.6 | 8.2 | 0.2 | 2.6 | 1.1 | 13.0 | 1.3 | 0.7 |

TABLE 3-continued

Performance of 17 genotypes in a replicated trial planted in Corvallis in Spring, 2014. Four trees per selection in a randomized complete block design.

| | | | | | | | | | |
|---|---|---|---|---|---|---|---|---|---|
| 10 | '1308.087' | 76.7 | 6.8 | 0.0 | 1.8 | 5.5 | 5.7 | 0.1 | 0.3 |
| 11 | '1310.022' | 86.9 | 3.4 | 0.1 | 0.5 | 0.5 | 1.7 | 6.0 | 1.9 |
| 12 | '1339.074' | 81.7 | 4.9 | 0.7 | 1.4 | 1.2 | 10.3 | 0.3 | 0.2 |
| 13 | '1340.018' | 73.0 | 4.8 | 0.3 | 2.1 | 3.4 | 16.3 | 0.1 | 0.2 |
| 14 | '1341.037' | 88.2 | 2.6 | 1.0 | 2.6 | 1.8 | 3.1 | 0.5 | 0.5 |
| 15 | 'Jefferson' | 76.5 | 3.8 | 2.0 | 2.2 | 1.3 | 13.8 | 0.6 | 1.0 |
| 16 | 'McDonald' | 86.0 | 3.8 | 0.5 | 2.3 | 4.0 | 3.3 | 0.1 | 0.0 |
| 17 | 'Wepster' | 80.3 | 7.6 | 0.2 | 1.3 | 0.7 | 8.7 | 0.0 | 1.4 |
| | LSD (0.05) | 3.0 | 1.9 | 0.8 | 1.2 | 1.4 | 1.7 | 0.6 | 0.8 |

Weight of ten well-filled nuts, and ten kernels in grams.

Percent kernel = (kernel weight/nut weight)'100, based on well-filled nuts.

Fiber on the kernel pellicle is rated from 1 (none) to 4 (heavy fiber).

Blanching (pellicle removal) is rated from 1 (complete pellicle removal) to 7 (no pellicle removal) after roasting at 275° F. for 15-20 minutes and rubbing.

Frequency of good nuts and 7 types of defects is from two 50-nut samples per tree, averaged over four trees and three years of observation. GD = good kernels, BL = blanks, BS = brown stain, MO = moldy kernels, SH = shriveled kernels, PF = poorly filled nuts, TW = twins, and BT = kernels with black tips.

Nut maturity date. The nuts of 'OSU 541.147' are typically borne in clusters of 3-4 in husks about 60% longer than the nuts. The husks open as they dry at maturity. About 85% of the nuts fall free of the husk at maturity (range 75-90%). The other 15% of the nuts come out of the husks as they move through the harvester. When mature, the shells are medium brown in color (165A). Harvest date on average is a few days later than 'Jefferson' when grown in East Brunswick, N.J., and Corvallis, Oreg. (Table 4).

Incompatibility and pollinizers. The trees set a moderate to high number of catkins that shed pollen in early season 2-3 days after to 'Yamhill'. Pollen has been collected and germinated on agar medium and both quantity and viability appear to be good. 'OSU 541.147' has incompatibility alleles $S_8$ and $S_{23}$ as determined by fluorescence microscopy. Both alleles are expressed in the female flowers but only $S_8$ is expressed in the pollen due to dominance. By convention, alleles expressed in the pollen are underlined.

TABLE 4

Harvest dates (2018 and 2019) in the replicated trial planted in Corvallis in 2014, and estimated percentage of nuts on the ground (vs. in the tree) on that date. Also shown for the nuts on the ground is an estimated percentage of nuts free of the husk.

| 2018 Harvest | | | | 2019 Harvest | | | |
|---|---|---|---|---|---|---|---|
| Selection | Date | % down | % free | Selection | Date | % down | % free |
| '05U541.147' | 10/5 | 76 | 80 | '541.147' | 10/7 | 82 | 88 |
| '1252.068' | 10/4 | 98 | 98 | '1252.068' | 10/3 | 93 | 91 |
| '1341.037' | 9/28 | 93 | 98 | '1341.037' | 9/23 | 99 | 97 |
| 'Barcelona' | 10/8 | 97 | 96 | 'Barcelona' | 10/8 | 99 | 94 |
| 'Jefferson' | 10/5 | 90 | 83 | 'Jefferson' | 10/7 | 94 | 84 |
| 'McDonald' | 9/20 | 92 | 97 | 'McDonald' | 9/23 | 99 | 97 |
| 'Wepster' | 10/5 | 99 | 96 | 'Wepster' | 9/23 | 96 | 76 |

In Corvallis, Oreg., time of pollen shed and female receptivity were recorded weekly from early December 2018 to late March 2019 (FIG. 6). Climatic conditions vary each year and impact dates of bloom but not usually the order of progression of bloom among cultivars. In 2019, pollen shed (time of male flowering) of 'OSU 541.147' began on January 25 and ended on February 25, with peak pollen shed on February 10; those dates are between those for 'Wepster' and 'PollyO'. The females reached the red dot stage on January 15 and remained receptive until February 15. Female receptivity spans a shorter time within the receptivity time of females of 'Wepster' and 'PollyO'. In East Brunswick, N.J., time of pollen shed and female receptivity were recorded weekly from early December 2017 to late March 2018 (FIG. 7) and from early December 2018 to late March 2019 (FIG. 8). Pollen shed of 'OSU 541.147' was about one week later than 'Jefferson' and ten days later than 'Yamhill'. Time of female receptivity overlapped the second half of 'Yamhill' and the first half of 'Jefferson'. Females emerge in early season and are generally fully receptive around mid-February in New Jersey. Pollinizer cultivars that shed compatible pollen in midseason and late midseason are recommended, with hybrid hazelnut seedlings (*Corylus americana* x *C. avellana*) planted as pollenizers in eastern and northern regions where cold temperatures and fluctuating climatic conditions can affect pollen production of *C. avellana*. In New Jersey, date of leaf budbreak of 'OSU 541.147' was four days later than 'Yamhill' and seven days earlier than 'Jefferson'. In Oregon, date of leaf budbreak of 'OSU 541.147' was with 'PollyO', one day before 'McDonald' and four days before 'Wepster'.

Propagation. Layers of 'OSU 541.147' are vigorous and root well, similar to standard cultivars of *Corylus avellana*.

Additional comparative descriptors. Tables 5 and 6 provide additional descriptors distinguishing 'OSU 541.147' from various hazelnut varieties.

TABLE 5

Additional comparative descriptors distinguishing 'OSU 541.147' from various hazelnut varieties, including measurements and RHS colors (R.H.S. Colour chart, 1966 edition. Royal Horticultural Society (Great Britain). British Colour Council, London).

| Character | Unit | 'OSU 541.147' | 'PollyO' | 'McDonald' |
|---|---|---|---|---|
| Lateral branch length (terminal shoot) | cm | 20.4 | 45.6 | 33.5 |
| Lateral branch diameter (terminal shoot) | mm | 4.3 | 4.4 | 5.0 |
| Internode length (above base) | cm | 3.6 | 3.4 | 3.2 |
| Branch texture | | smooth, glabrous | smooth. glabrous | smooth, glabrous |
| Branch strength | | strong | strong | strong |
| Branch color, immature | RHS | 143C | 139D | 139D |
| Branch color, mature | RHS | 146B | 177D | 177D |
| Leaf length | cm | 9.6 | 13.3 | 10.4 |
| Leaf width | cm | 7.1 | 11.8 | 8.7 |
| Leaf shape | | oblong to ovate | oblong to ovate | oblong to ovate |
| Leaf apex | | obtuse to acute | obtuse to acute | obtuse to acute |
| Leaf base | | cordate | cordate | cordate |
| Leaf margin | | serrate | senate | serrate |
| Leaf texture | | slightly pubescent | slightly pubescent | slightly pubescent |
| Leaf venation pattern | | pinnate | pinnate | pinnate |
| Leaf color developing leaf upper | RHS | 144 A | 141C | 141C |
| Leaf color developing leaf lower | RHS | 144B | 139C | 139C |
| Leaf color fully expanded leaf upper, Spr Sum | RHS | 137B | 146 A | 139B |
| Leaf color fully expanded leaf upper, ea Fall | RHS | 137B | 146 A | 139B |
| Leaf color fully expanded leaf lower, Spr Sum | RHS | 137D | 146B | 139C |
| Leaf color fully expanded leaf lower, ea Fall | RHS | 137D | 146B | 139C |
| Leaf veins, upper. Spring Summer | RHS | 145 A | 146 A | 139C |
| Leaf veins, upper, ea Fall | RHS | 145 A | 146 A | 139C |

TABLE 5-continued

Additional comparative descriptors distinguishing 'OSU 541.147' from various hazelnut varieties, including measurements and RHS colors (R.H.S. Colour chart, 1966 edition. Royal Horticultural Society (Great Britain). British Colour Council, London).

| | | | | |
|---|---|---|---|---|
| Leaf veins, lower. Spring Summer | RHS | 145 A | 146D | 139D |
| Leaf veins, lower, ea Fall | RHS | 145 A | 146D | 139D |
| Petiole length | mm | 9.3 | 16.3 | 27 |
| Petiole diameter | mm | 1.8 | 1.6 | 1.8 |
| Petiole texture, upper & lower surfaces | | pubescent | pubescent | pubescent |
| Petiole color, upper. Spring Summer | RHS | 143C | 146C | 139D |
| Petiole color, upper, ea Fall | RHS | 143C | 146C | 139D |
| Petiole color, lower, Spring Summer | RHS | 143C | 146D | 139D |
| Petiole color, lower, ea Fall | RHS | 143C | 146D | 139D |
| Catkin color prior to elongation | RHS | ND | 138B | 176D |
| Female flower style color | RHS | 047B | 047B | 047B |
| Nut length | mm | 19.9 | 19.5 | 18.4 |
| Nut width | mm | 18.8 | 19.8 | 18.9 |
| Nut depth | mm | 15.6 | 17.2 | 17.9 |
| Nut shape | | round | round | round |
| Nut shape index [(W + D)/2L] | ratio | 0.86 | 0.95 | 1.00 |
| Nut compression index (W/D) | ratio | 1.21 | 1.15 | 1.05 |
| Nut shell color | RHS | 165A | 164 A | 164 A |
| Nut weight | g | 2.62 | 2.88 | 2.51 |
| Kernel weight | g | 1.16 | 1.38 | 1.29 |
| Kernel percentage (KW/NW) | % | 44.1 | 47.9 | 51.5 |

| Character | Unit | 'Wepster' | 'Felix' | 'York' |
|---|---|---|---|---|
| Lateral branch length (terminal shoot) | cm | 40 | 43 | 38 |
| Lateral branch diameter (terminal shoot) | mm | 5.4 | 6.0 | 6.0 |
| Internode length (above base) | cm | 3.1 | 2.8 | 3.2 |
| Branch texture | | smooth, glabrous | smooth, glabrous | smooth, glabrous |
| Branch strength | | strong | strong | strong |
| Branch color, immature | RHS | 139D | 152B | 152B |
| Branch color, mature | RHS | 177C | 152B | 199A? |
| Leaf length | cm | 12.1 | 11 | 11 |
| Leaf width | cm | 10.9 | 10 | 10 |
| Leaf shape | | oblong to ovate | oblong to ovate | oblong to ovate |
| Leaf apex | | obtuse to acute | obtuse to acute | obtuse to acute |
| Leaf base | | cordate | cordate | cordate |
| Leaf margin | | serrate | senate | serrate |
| Leaf texture | | slightly pubescent | slightly pubescent | slightly pubescent |
| Leaf venation pattern | | pinnate | pinnate | pinnate |
| Leaf color developing leaf upper | RHS | 141C | 144 A | 146B |
| Leaf color developing leaf lower | RHS | 139C | 145 A | 146C |
| Leaf color fully expanded leaf upper, Spr Sum | RHS | 141B | 143 A | 146 A |
| Leaf color fully expanded leaf upper, ea Fall | RHS | 141A | 143 A | 146 A |
| Leaf color fully expanded leaf lower, Spr Sum | RHS | 139C | 139C | 146C |
| Leaf color fully expanded leaf lower, ea Fall | RHS | 139C | 139C | 146C |
| Leaf veins, upper. Spring Summer | RHS | 139C | 139C | 146A |
| Leaf veins, upper, ea Fall | RHS | 139C | 139C | 146 A |
| Leaf veins, lower. Spring Summer | RHS | 139D | 139D | 148D |
| Leaf veins, lower, ea Fall | RHS | 139D | 139D | 148D |
| Petiole length | mm | 27 | 27 | 27 |
| Petiole diameter | mm | 1.8 | 1.8 | 1.8 |
| Petiole texture, upper & lower surfaces | | pubescent | pubescent | pubescent |

TABLE 5-continued

Additional comparative descriptors distinguishing 'OSU 541.147' from various hazelnut varieties, including measurements and RHS colors (R.H.S. Colour chart, 1966 edition. Royal Horticultural Society (Great Britain). British Colour Council, London).

| | | | | |
|---|---|---|---|---|
| Petiole color, upper. Spring Summer | RHS | 139D | 139D | 139D |
| Petiole color, upper, ea Fall | RHS | 139D | 139D | 139D |
| Petiole color, lower, Spring Summer | RHS | 139D | 139D | 139D |
| Petiole color, lower, ea Fall | RHS | 139D | 139D | 139D |
| Catkin color prior to elongation | RHS | 176C | 194C shade, 176D sun | 194C |
| Female flower style color | RHS | 047B | 047B | 047B |
| Nut length | mm | 18.3 | 18.7 | 18.0 |
| Nut width | mm | 19.0 | 18.9 | 19.7 |
| Nut depth | mm | 16.6 | 16.7 | 17.0 |
| Nut shape | | round | round | round |
| Nut shape index [(W + D)/2L] | ratio | 0.97 | 0.95 | 1.02 |
| Nut compression index (W/D) | ratio | 1.15 | 1.13 | 1.16 |
| Nut shell color | RHS | 164 A | 167 A | 164 A |
| Nut weight | g | 2.39 | 2.65 | 2.73 |
| Kernel weight | g | 1.11 | 1.32 | 1.23 |
| Kernel percentage (KW/NW) | % | 43.9 | 50.1 | 46.3 |

| Character | Unit | 'Dorris' | 'Tonda Pacifica' | 'Burgundy Lace' |
|---|---|---|---|---|
| Lateral branch length (terminal shoot) | cm | 51 | 15 | 51 |
| Lateral branch diameter (terminal shoot) | mm | 3.8 | 5.0 | 3.8 |
| Internode length (above base) | cm | 3.3 | 1.3 | 3.3 |
| Branch texture | | smooth, glabrous | smooth, glabrous | smooth, glabrous |
| Branch strength | | strong | strong | strong |
| Branch color, immature | RHS | 152B | 178 A | 177D |
| Branch color, mature | RHS | 152B | 137 A | 177C |
| Leaf length | cm | 11 | 12 | 10.7 |
| Leaf width | cm | 10 | 10 | 7.8 |
| Leaf shape | | oblong to ovate | oblong to ovate | oblong to ovate |
| Leaf apex | | obtuse to acute | obtuse to acute | obtuse to acute |
| Leaf base | | cordate | cordate | cordate |
| Leaf margin | | serrate | serrate | serrate |
| Leaf texture | | slightly pubescent | slightly pubescent | slightly pubescent |
| Leaf venation pattern | | pinnate | pinnate | pinnate |
| Leaf color developing leaf upper | RHS | 144 A | 187 A | 187 A |
| Leaf color developing leaf lower | RHS | 145 A | 187 A | 183 A |
| Leaf color fully expanded leaf upper, Spr Sum | RHS | 143 A | 183B | 191A |
| Leaf color fully expanded leaf upper, ea Fall | RHS | 143 A | 137 A | 191B |
| Leaf color fully expanded leaf lower, Spr Sum | RHS | 139C | 178 A | 191B |
| Leaf color fully expanded leaf lower, ea Fall | RHS | 139C | 137 A | 139B |
| Leaf veins, upper. Spring Summer | RHS | 139C | 183B | 191A |
| Leaf veins, upper, ea Fall | RHS | 139C | 137 A | 139C |
| Leaf veins, lower. Spring Summer | RHS | 139D | 178 A | 182B |
| Leaf veins, lower, ea Fall | RHS | 139D | 138B | 182D |
| Petiole length | mm | 27 | 10 | 27 |
| Petiole diameter | mm | 1.8 | 2.5 | 1.8 |
| Petiole texture, upper & lower surfaces | | pubescent | pubescent | pubescent |
| Petiole color, upper. Spring Summer | RHS | 139D | 183B | 191A |
| Petiole color, upper, ea Fall | RHS | 139D | 137 A | 139C |
| Petiole color, lower, Spring Summer | RHS | 139D | 178 A | 191A |

TABLE 5-continued

Additional comparative descriptors distinguishing 'OSU 541.147' from various hazelnut varieties, including measurements and RHS colors (R.H.S. Colour chart, 1966 edition. Royal Horticultural Society (Great Britain). British Colour Council, London).

| | | | | |
|---|---|---|---|---|
| Petiole color, lower, ea Fall | RHS | 139D | 138B | 139C |
| Catkin color prior to elongation | RHS | 194C shade, 176D sun | 176B | 177 A |
| Female flower style color | RHS | 048B | 183B | 183B |
| Nut length | mm | 19.1 | 19.0 | 15.8 |
| Nut width | mm | 20.7 | 18.0 | 15.6 |
| Nut depth | mm | 18.2 | 16.5 | 12.9 |
| Nut shape | | round | round | round |
| Nut shape index [(W + D)/2L] | ratio | 1.02 | 0.91 | 0.85 |
| Nut compression index (W/D) | ratio | 1.14 | 1.09 | 1.21 |
| Nut shell color | RHS | 164B | 164 A | 166C |
| Nut weight | g | 3.35 | 2.24 | 1.72 |
| Kernel weight | g | 1.40 | 1.06 | 0.76 |
| Kernel percentage (KW/NW) | % | 43 | 47 | 44 |

TABLE 6

International Union for the Protection of New Varieties of Plants (UPOV) descriptors distinguishing 'OSU 541.147' from various hazelnut varieties.

| No. | Character (UPOV Descriptor) | 'OSU 541.147' | 'PollyO' | 'Burgundy Lace' | 'Dorris' |
|---|---|---|---|---|---|
| 1 | Plant vigor | 5 | 7 | 5 | 4 |
| 2 | Plant habit | 1 | 5 | 5 | 7 |
| 3 | Plant shoot density | 5 | 5 | 5 | 5 |
| 4 | Plant suckering | 5 | 4 | 5 | 4 |
| 5 | Shoot thickness | 5 | 7 | 5 | 7 |
| 6 | Shoot hairiness | 7 | 3 | 3 | 5 |
| 7 | Shoot lenticels | 7 | 5 | 3 | 3 |
| 8 | Leaf bud shape (winter) | Ovoid; 2 | 2 | 1 | 3 |
| 9 | Leaf bud color (winter) | Reddish green; 2 | 143C,1 | 3 | 2 |
| 10 | Time of leaf budburst | 6 | 6 | 6 | 6 |
| 11 | Catkin length (mm) (winter) | 20.1 mm; 3 | 20.1; 3 | 2 | 8 |
| 12 | Catkin color (winter) | 138B; 1 | 138B.1 | 2 | 2 |
| 13 | Stigma color | 2 | 047B.1 | 3 | 2 |
| 14 | Time of pollen shed | 6 | 7 | 6 | 5 |
| 15 | Time of female flowering | 6 | 6 | 8 | 6 |
| 16 | Dichogamy (female vs. male) | 2 | 2 | 3 | 2 |
| 17 | Leaf blade shape | 2 | 3 | 2 | 3 |
| 18 | Leaf blade size | 9.6 × 7.1; 3 | 13.3 × 11.8;5 | 11.4 × 7.4; 1 | 7 |
| 19 | Leaf blade hairiness lower side | 3 | 3 | | 3 |
| 20 | Petiole length | 9.3 mm; 3 | 5 | 7 | 5 |
| 21 | Petiole hairiness | 7 | 3 | 3 | 5 |
| 22 | Husk constriction | 1 | 1 | 1 | 1 |
| 23 | Husk length rcl. to nut length | 6 | 6 | 3 | 4 |
| 24 | Husk indentation | 7 | 5 | 5 | 7 |
| 25 | Husk serration of indentations | 5 | 5 | 3 | 5 |
| 26 | Husk thickness of callus at base | 7 | 7 | 3 | 7 |
| 27 | Husk hairiness (present, absent) | 9 | 9 | 1 | 9 |
| 28 | Husk hair density | 8 | 3 | 3 | 3 |
| 29 | Husk joining of bracts | 1 | 1 | 1 | 2 |
| 30 | Nuts per cluster | 4 | 4 | 2 | 3 |
| 31 | Nut size | 3 | 4 | 2 | 5 |
| 32 | Nut shape | 3 | 1 | 3 | 1 |
| 33 | Nut shape in cross-section | 2 | 2 | 1 | 2 |
| 34 | Nut shell color | 3 | 2 | 3 | 2 |
| 35 | Nut number of stripes on shell | 7 | 3 | 5 | 3 |
| 36 | Nut shape of top | 1 | 1 | 4 | 4 |
| 37 | Nut apex prominence | 7 | 3 | 3 | 3 |

TABLE 6-continued

International Union for the Protection of New Varieties of Plants (UPOV) descriptors distinguishing 'OSU 541.147' from various hazelnut varieties.

| | | | | | |
|---|---|---|---|---|---|
| 38 | Nut size of pistil scar | 3 | 3 | 3 | 3 |
| 39 | Nut hairiness of top | 3 | 4 | 5 | 4 |
| 40 | Nut size of basal scar | 5 | 3 | 3 | 5 |
| 41 | Nut curvature of basal scar | 3 | 2 | 3 | 2 |
| 42 | Double kernels (frequency) | 1 | 1 | 1 | 1 |
| 43 | Kernel size | 3 | 5 | 2 | 6 |
| 44 | Kernel shape | 1 | 1 | 2 | 1 |
| 43 | Kernel cross-section | 2 | 2 | 1 | 2 |
| 46 | Kernel shape of top | 2 | 2 | 2 | 2 |
| 47 | Kernel shape of base | 3 | 3 | 2 | 3 |
| 48 | Kernel lateral groove | 1 | 1 | 1 | 1 |
| 49 | Kernel fiber on skin | 9 | 5 | 5 | 3 |
| 50 | Kernel size of cavity | 5 | 5 | 3 | 7 |
| 51 | Nut ripening time | 7 | 4 | 5 | 6 |
| 52 | Nut adherence of husk after drop | 1 | 1 | 1 | 1 |
| 53 | Nut percent kernel | 3 | 6 | 3 | 3 |
| 54 | Time of leaf fall (November) | 3 | 3 | 3 | 3 |

| No. | Character (UPOV Descriptor) | 'York' | 'Felix' | 'Wep-ster' | 'McDonald' |
|---|---|---|---|---|---|
| 1 | Plant vigor | 5 | 8 | 7 | 5 |
| 2 | Plant habit | 5 | 3 | 5 | 5 |
| 3 | Plant shoot density | 5 | 5 | 5 | 5 |
| 4 | Plant suckering | 4 | 5 | 3 | 6 |
| 5 | Shoot thickness | 7 | 7 | 5 | 5 |
| 6 | Shoot hairiness | 3 | 3 | 5 | 3 |
| 7 | Shoot lenticels | 5 | 3 | | |
| 8 | Leaf bud shape (winter) | 3 | 2 | | |
| 9 | Leaf bud color (winter) | 1 | 2 | | |
| 10 | Time of leaf budburst | 6 | 6 | 6 | 6 |
| 11 | Catkin length (mm) (winter) | 7 | 7 | 5 | 6 |
| 12 | Catkin color (winter) | 2 | 2 | 1 | 1 |
| 13 | Stigma color | 1 | 1 | 1 | 1 |
| 14 | Time of pollen shed | 6 | 7 | 6 | 5 |
| 15 | Time of female flowering | 5 | 5 | 5 | 4 |
| 16 | Dichogamy (female vs. male) | 2 | 1 | 1 | 1 |
| 17 | Leaf blade shape | 3 | 3 | 3 | 2 |
| 18 | Leaf blade size | 3 | 2 | 3 | 3 |
| 19 | Leaf blade hairiness lower side | 3 | 3 | 3 | 3 |
| 20 | Petiole length | 5 | 5 | 5 | 5 |
| 21 | Petiole hairiness | 5 | 5 | 5 | 5 |
| 22 | Husk constriction | 1 | 3 | 1 | 1 |
| 23 | Husk length rel. to nut length | 4 | 5 | 7 | 5 |
| 24 | Husk indentation | 7 | 5 | 7 | 7 |
| 25 | Husk serration of indentations | 5 | 7 | 7 | 7 |
| 26 | Husk thickness of callus at base | 5 | 7 | 5 | 3 |
| 27 | Husk hairiness (present, absent) | 9 | 9 | 9 | 9 |
| 28 | Husk hair density | 3 | 3 | 3 | 3 |
| 29 | Husk joining of bracts | 2 | 2 | 2 | 2 |
| 30 | Nuts per cluster | 2 | 3 | 3 | 3 |
| 31 | Nut size | 4 | 4 | 3 | 4 |
| 32 | Nut shape | 1 | 1 | 1 | 1 |
| 33 | Nut shape in cross-section | 2 | 2 | 2 | 2 |
| 34 | Nut shell color | 2 | 3 | 2 | 2 |
| 35 | Nut number of stripes on shell | 5 | 7 | 5 | 5 |
| 36 | Nut shape of top | 3 | 1 | 1 | 3 |
| 37 | Nut apex prominence | 3 | 5 | 3 | 5 |
| 38 | Nut size of pistil scar | 3 | 3 | 3 | 3 |
| 39 | Nut hairiness of top | 3 | 4 | 3 | 4 |
| 40 | Nut size of basal scar | 3 | 3 | 3 | 3 |
| 41 | Nut curvature of basal scar | 2 | 2 | 2 | 2 |
| 42 | Double kernels (frequency) | 1 | I | 1 | 1 |

TABLE 6-continued

International Union for the Protection of New Varieties of Plants (UPOV) descriptors distinguishing 'OSU 541.147' from various hazelnut varieties.

| | | | | | |
|---|---|---|---|---|---|
| 43 | Kernel size | 5 | 5 | 3 | 5 |
| 44 | Kernel shape | 1 | 1 | 1 | 1 |
| 43 | Kernel cross-section | 2 | 2 | 2 | 2 |
| 46 | Kernel shape of top | 2 | 2 | 3 | 1 |
| 47 | Kernel shape of base | 3 | 3 | 3 | 3 |
| 48 | Kernel lateral groove | 1 | 1 | 1 | 1 |
| 49 | Kernel fiber on skin | 5 | 6 | 5 | 5 |
| 50 | Kernel size of cavity | 5 | 7 | 5 | 7 |
| 51 | Nut ripening time | 5 | 6 | 5 | 4 |

TABLE 6-continued

International Union for the Protection of New Varieties of Plants (UPOV) descriptors distinguishing 'OSU 541.147' from various hazelnut varieties.

| | | | | | |
|---|---|---|---|---|---|
| 52 | Nut adherence of husk after drop | 1 | 3 | 1 | 1 |
| 53 | Nut percent kernel | 4 | 5 | 4 | 6 |
| 54 | Time of leaf fall (November) | 4 | 7 | 4 | 4 |

Microsatellite Marker Analysis: Twenty microsatellite (simple sequence repeat) markers were used. PCR products were multiplexed post-PCR and sized using capillary electrophoresis (Table 6, and see for example Bassil et al., *Acta Horticulturae* 686:105-110, 2005; Gökirmak et al., *Genetic Resources and Crop Evolution* 56:147-172, 2009; Gürcan and Mehlenbacher. *Molecular Breeding* 26:551-559, 2010; Gürcan et al.. *Tree Genetics and Genomes* 6:513-531, 2010).

TABLE 7

Primers and annealing temperatures for the microsatellite marker loci used for fingerprinting hazelnut cultivars.

| Set | Locus | Repeat Motif | Allele sizes | Primers (5'-3') (SEQ ID NO:) | (SEQ ID NO:) | Tm (° C.) | n | He | Ho | PIC | r | LG | Locus | Reference |
|---|---|---|---|---|---|---|---|---|---|---|---|---|---|---|
| 3 | A613 | $(TC)_{132}$ $(CA)_{1}$ | 149-177 | Ned-CACACGCCTTGTCACTCTTT (1) | R-CCCCTTTCACATGTTTGCTT( 2) | 60 | 14 | 0.86 | 0.85 | 0.85 | 0.00 | 11R | A613 | Gurcan et al., 2010 |
| 2 | A614 | $(TC)_{17}$ $(CA)_{10}$ $NNN(CA)_{6}$ | 125-156 | Hex-TGGCAGAGCTTTGTCAGCTT (3) | R-GCAGTGGAGGATTGCTGACT (4) | 60 | 14 | 0.85 | 0.85 | 0.84 | 0.00 | 6S, 6R | A614 | Gurcan et al., 2010 |
| 3 | A616 | $(AC)_{11}$ | 136-162 | Fam-CACTCATACCGCAAACTCCA (5) | R-ATGGCTTTTGCTTCGTTTTG (6) | 60 | 13 | 0.85 | 0.85 | 0.83 | 0.00 | 8R | A616 | Gurcan et al., 2010 |
| 1 | A640 | $(CT)_{153}$ $(CA)_{1}$ | 354-378 | F-TGCCTCTGCAGTTAGTCATCAAATGTAGG (7) | Fam-CGCCATATAATTGGGATGCTTGTTG (8) | 67 | 11 | 0.80 | 0.73 | 0.77 | 0.04 | 10R | A640 | Gurcan et al., 2010 |
| 3 | B617 | $(GA)_{15}$ | 280-298 | Fam-TCCGTGTTGAGTATGGACGA (9) | R-TGTTTTTGGTGGAGCGATG (10) | 60 | 9 | 0.80 | 0.78 | 0.78 | 0.01 | 8S, 8R | B617 | Gurcan et al., 2010 |
| 2 | B619 | $(TC)_{21}$ | 146-180 | Fam-AGTCGGCTCCCCTTTTCTC(11) | R-GCGATCTGACCTCATTTTTG (12) | 60 | 14 | 0.88 | 0.88 | 0.87 | 0.00 | 3S, 3R | B619 | Gurcan et al., 2010 |
| 4 | B634 | $(AG)_{15}$ | 218-238 | Hex-CCTGCATCCAGGACTCATTA (13) | R-GTGCAGAGGTTGCACTCAAA (14) | 60 | 9 | 0.76 | 0.76 | 0.73 | 0.00 | 4R | B634 | Gurcan et al., 2010 |
| 4 | B657 | $(AG)_{15}$ | 210-228 | Ned-GAGAGTGCGTCTTCCTCTGG (15) | R-AGCCTCACCTCCAACGAAC (16) | 60 | 8 | 0.84 | 0.98 | 0.82 | −0.08 | 11S, 11R | B657 | Gurcan et al., 2010 |
| 3 | B671 | $(AG)_{6}NN$ $(GA)_{17}$ | 221-249 | Hex-TTGCCAGTGCATACTCTGATG (17) | R-ACCAGCTCTGGGCTTAACAC (18) | 60 | 13 | 0.86 | 0.88 | 0.84 | −0.01 | 9S, 9R | B671 | Gurcan et al., 2010 |
| 2 | B709 | $(GA)_{21}$ | 219-233 | Ned-CCAAGCACGAATGAACTCAA (19) | R-GCGGGTTCTCGTTGTACACT (20) | 60 | 8 | 0.74 | 0.76 | 0.70 | −0.01 | 5S, 5R | B709 | Gurcan et al., 2010 |
| 1 | B733 | $(TC)_{15}$ | 161-183 | Ned-CACCCTCTTCACCACCTCAT (21) | R-CATCCCCTGTTGGAGTTTTC (22) | 60 | 8 | 0.68 | 0.68 | 0.63 | 0.00 | 7S, 2R | B733 | Gurcan et al., 2010 |

TABLE 7-continued

Primers and annealing temperatures for the microsatellite marker loci used for fingerprinting hazelnut cultivars.

| Set | Locus | Repeat Motif | Allele sizes | Primers (5'-3') (SEQ ID NO:) | (SEQ ID NO:) | Tm (° C.) | n | He | Ho | PIC | r | LG | Locus | Reference |
|---|---|---|---|---|---|---|---|---|---|---|---|---|---|---|
| 2 | B749 | $(TC)_{12}$ | 200-210 | Hex-GGCTGACAACACAGCAGAAA (23) | R-TCGGCTAGGTGTAGGGTTTT (24) | 60 | 6 | 0.60 | 0.64 | 0.51 | −0.03 | 1R | B749 | Gurcan et al., 2010 |
| 4 | B751 | $(GA)_{15}$ | 141-153 | Fam-AGCTGGTTCTTCGACATTCC (25) | R-AAACTCAAATAAAACCCCTGCTC(26) | 60 | 7 | 0.80 | 0.78 | 0.77 | 0.01 | 7S, 2R | B751 | Gurcan et al., 2010 |
| 1 | B774 | $(AG)_{15}$ | 195-213 | Ned-GTTTTGCGAGCTCATTGTCA (27) | R-TGTGTGTGGTCTGTAGGCACT (28) | 60 | 8 | 0.80 | 0.80 | 0.77 | 0.00 | 5S, 5R | B774 | Gurcan et al., 2010 |
| 3 | C115 | $(TAA)_5$ $(GAA)_{12}$ | 167-225 | Fam-CATTTTCCGCAGATAATACAGG (29) | R-GTTTCCAGATCTGCCTCCATATAAT (30) | 60 | 10 | 0.84 | 0.90 | 0.82 | 0.035 | 4S, 4R | C115 | Bassil et al., 2005b; Gokirmak et al., 2009 |
| 3 | KG807 | (TAAA)AA $(TAAA)_2$A $(TAAA)_2$ | 226-248 | F-AAGCAAGAAAGGGATGGT (31) | Fam-CTTACAGATAAATGGCTCAAA (32) | 54 | 4 | 0.67 | 0.78 | 0.60 | −0.07 | 11 | KG807 | Gurcan and Mehlenbacher, 2010 |
| 1 | KG809 | $(AGG)_6$ | 333-345 | F-GGAAGGTGAGAGAAATCAAGT (33) | Hex-AGGCATCAGTTCATCCAA (34) | 55 | 5 | 0.66 | 0.64 | 0.60 | 0.01 | 4 | KG809 | Gurcan and Mehlenbacher, 2010 |
| 2 | KG811 | $(GA)_{17}$ | 240-278 | F-GAACAACTGAAGACAGCAAAG (35) | Ned-AAGGCGGCACTCGCTCAC (36) | 58 | 12 | 0.83 | 0.82 | 0.81 | 0.01 | 2 | KG811 | Gurcan and Mehlenbacher, 2010 |
| 4 | KG827 | $(CT)_{13}$AA $(CA)_7$ | 264-282 | Fam-AGAACTCCGACTAATAATCCTAACCCTTGC (37) | R-GAGGGAGCAAGTCAAAGTTGAGAAGAAA( 38) | 67 | 9 | 0.78 | 0.84 | 0.75 | −0.04 | 9 | KG827 | Gurcan and Mehlenbacher, 2010 |
| 2 | KG830 | $(CT)_{14}$ GTATT $(CA)_8$ | 279-311 | Ned-TGGAGGAAGTTTTGAATGGTAGTAGAGGA (39) | R-AAAGCAACTCATAGCTGAAGTCCAATC (40)A | 67 | 9 | 0.79 | 0.78 | 0.76 | 0.00 | 9 | KG830 | Gurcan and Mehlenbacher, 2010 |

Set = Multiplex set, with samples mixed after PCR but before submission for sizing by capillary electrophoresis;
Allele size = range of sizes;
Primers, forward (F, listed first) and reverse (R, second) (Hex and Fam are dyes);
Tm = Annealing temperature;
n = Number of alleles;
He = expected heterozygosity;
Ho = observed heterozygosity;
PIC = Polymorphism information content;
r = frequency of null alleles;
LG = linkage group (S is susceptible female parent 'OSU 252.146'; R is resistant parent 'OSU 414.062');
Reference is the journal article where additional details were published.

Table 8 shows allele sizes at 20 microsatellite markers for 'OSU 541.147', its female parent 'NY 616', and 13 additional cultivars and selections. 'Rush', 'Barcelona', 'Montebello' and 'Tombul Ghiaghli' are in the pedigree of 'OSU 541.147'. Cultivars 'OSU 541.147', 'NY 110', 'NY 616', 'Rush', 'Barcelona' , 'Montebello', and 'Tombul Ghiaghli' were fingerprinted in 2020. The other cultivars were fingerprinted in 2018 for 'PollyO' (U.S. Plant Patent Publication No. US-2020-0008334-P1). 'OSU 541.147' is easily distinguished from all others shown in Table 8. 'OSU 541.147' shares an allele with its mother 'NY 616' at all SSR loci.

TABLE 8

Allele sizes at 20 microsatellite markers

| Marker | 'OSU 541.147' | 'NY 616' | 'Rush' | 'Barcelona' | 'Montebello' | 'Tombul Ghiaghli' |
|---|---|---|---|---|---|---|
| A613 | 161/161 | 161/163 | 153/163 | 153/161 | 151/153 | 153/169 |
| A614 | 124/150 | 124/132 | 124/133 | 124/132 | 124/132 | 132/150 |
| A616 | 144/150 | 144/150 | 140/150 | 144/152 | 152/160 | 152/160 |
| A640 | 356/374 | 356/356 | 356/356 | 354/374 | 362/374 | 354/374 |
| B617 | 289/289 | 281/289 | 281/285 | 285/289 | 285/293 | 293/295 |
| B619 | 158/170 | 158/172 | 158/168 | 158/172 | 160/166 | 166/170 |

TABLE 8-continued

| Allele sizes at 20 microsatellite markers | | | | | | |
|---|---|---|---|---|---|---|
| B634 | 228/228 | 228/240 | 230/240 | 228/228 | 232/236 | 228/232 |
| B657 | 222/222 | 214/222 | 214/214 | 218/222 | 218/226 | 210/214 |
| B671 | 225/249 | 225/231 | 231/231 | 225/229 | 225/243 | 229/249 |
| B709 | 229/235 | 229/235 | 229/229 | 227/235 | 229/235 | 223/229 |
| B733 | 173/175 | 173/175 | 175/175 | 173/175 | 175/185 | 173/175 |
| B749 | 216/216 | 208/216 | 206/208 | 216/216 | 216/216 | 216/216 |
| B751 | 148/150 | 144/150 | 150/150 | 144/154 | 154/154 | 148/154 |
| B774 | 205/217 | 205/213 | 205/205 | 209/213 | 209/213 | 201/217 |
| C115 | 182/215 | 174/215 | 215/215 | 174/194 | 174/197 | 174/182 |
| KG807 | 252/252 | 242/252 | 238/242 | 238/252 | 238/242 | 230/253 |
| KG809 | 339/342 | 339/339 | 339/339 | 339/339 | 339/348 | 339/342 |
| KG811 | 263/267 | 263/267 | 255/263 | 261/267 | 251/267 | 245/267 |
| KG827 | 278/282 | 270/282 | 270/272 | 282/284 | 282/282 | 278/284 |
| KG830 | 291/295 | 291/307 | 307/307 | 291/295 | 291/295 | 289/295 |

| Marker | 'NY 110' | 'Daviana' | 'Mortarella' | 'Negret' | 'Casina' |
|---|---|---|---|---|---|
| A613 | 153/163 | 167/179 | 151/153 | 153/159 | 151/153 |
| A614 | 124/132 | 148/150 | 132/135 | 132/132 | 124/139 |
| A616 | 140/150 | 150/152 | 150/158 | 152/160 | 144/152 |
| A640 | 356/374 | 354/354 | 354/374 | 354/368 | 354/372 |
| B617 | 285/293 | 289/295 | 293/295 | 285/291 | 285/295 |
| B619 | 168/168 | 168/178 | 158/172 | 166/170 | 150/158 |
| B634 | 232/240 | 228/236 | 228/236 | 228/234 | 228/232 |
| B657 | 214/218 | 218/226 | 218/224 | 218/222 | 216/218 |
| B671 | 229/231 | 239/249 | 225/243 | 229/237 | 229/249 |
| B709 | 229/229 | 229/229 | 221/229 | 223/227 | 227/233 |
| B733 | 163/175 | 173/181 | 175/175 | 167/175 | 175/175 |
| B749 | 208/216 | 216/216 | 214/216 | 216/216 | 214/216 |
| B751 | 144/150 | 144/152 | 144/154 | 152/154 | 152/154 |
| B774 | 205/209 | 213/215 | 209/220 | 209/215 | 209/215 |
| C115 | 174/215 | 174/194 | 182/215 | 182/215 | 174/197 |
| KG807 | 242/242 | 238/252 | 230/234 | 238/252 | 238/252 |
| KG809 | 339/339 | 339/342 | 342/342 | 339/342 | 339/339 |
| KG811 | 255/263 | 255/261 | 261/267 | 259/267 | 251/267 |
| KG827 | 272/284 | 272/272 | 282/282 | 272/284 | 272/284 |
| KG830 | 295/295 | 289/295 | 291/307 | 295/303 | 295/303 |

| Marker | 'Polly0' | 'McDonald' | 'Wepster' | 'Yamhill' | 'Tonda Pacifica' |
|---|---|---|---|---|---|
| A613 | 153/167 | 153/169 | 159/167 | 153/163 | 159/169 |
| A614 | 124/158 | 135/158 | 135/158 | 132/158 | 135/150 |
| A616 | 144/152 | 150/160 | 152/160 | 150/150 | 150/160 |
| A640 | 354/354 | 362/368 | 368/374 | 354/368 | 368/374 |
| B617 | 285/295 | 293/295 | 293/295 | 289/295 | 293/295 |
| B619 | 158/166 | 158/172 | 166/172 | 158/172 | 166/172 |
| B634 | 228/236 | 222/228 | 228/228 | 236/236 | 228/228 |
| B657 | 218/218 | 210/218 | 226/226 | 218/228 | 210/226 |
| B671 | 229/249 | 229/237 | 239/249 | 225/243 | 229/239 |
| B709 | 223/227 | 229/229 | 229/235 | 229/229 | 229/235 |
| B733 | 175/181 | 173/175 | 173/175 | 181/185 | 173/175 |
| B749 | 216/216 | 214/216 | 214/216 | 216/216 | 214/216 |
| B751 | 144/154 | 144/144 | 144/144 | 152/152 | 144/154 |
| B774 | 209/209 | 209/220 | 209/213 | 209/217 | 209/213 |
| C115 | 194/215 | 174/197 | 182/194 | 197/215 | 174/182 |
| KG807 | 238/252 | 252/252 | 252/252 | 230/252 | 228/252 |
| KG809 | 342/342 | 339/339 | 342/342 | 348/348 | 339/342 |
| KG811 | 261/267 | 245/267 | 257/257 | 251/261 | 245/257 |
| KG827 | 272/284 | 272/284 | 270/282 | 282/282 | 270/284 |
| KG830 | 291/295 | 291/295 | 295/305 | 291/295 | 291/295 |

REFERENCES

Bhattarai, G., S. A. Mehlenbacher, and D. C. Smith. 2017. Eastern filbert blight disease resistance from *Corylus americana* 'Rush' and selection 'Yoder #5' maps to linkage group 7. Tree Genet. Genomes 13:45. DOI 10.1007/s11295-017-1129-9

Capik, J. M. and T. J. Molnar. 2012. Assessment of host (*Corylus* sp.) resistance to eastern filbert blight in New Jersey. J. Amer. Soc. Hort. Sci. 137:157-172.

Capik, J. M. and T. J. Molnar. 2014. Flowering phenology of eastern filbert blight-resistant accessions in New Jersey. HortTechnology 24:196-208.

Coyne, C. J., S. A. Mehlenbacher, and D. C. Smith. 1998. Sources of resistance to eastern filbert blight. J. Amer. Soc. Hort. Sci. 124:253-257.

Manzo, P. and G. Tamponi. 1982. Monografia di cultivar di nocciuolo. Istituto Sperimentale per la Frutticoltura, Roma.

Mehlenbacher, S. A. 2014. Geographic distribution of incompatibility alleles in cultivars and selections of European hazelnut. J. Amer. Soc. Hort. Sci. 139:191-212.

Mehlenbacher, S. A., M. M. Thompson, and H. R. Cameron. 1991a. Occurrence and inheritance of resistance to eastern filbert blight in 'Gasaway' hazelnut. HortScience 26:410-411.

Mehlenbacher, S. A., R. N. Brown, E. R. Nouhra, T. Gökirmak, N. V. Bassil, and T. L. Kubisiak. 2006. A genetic linkage map for hazelnut (*Corylus avellana* L.) based on RAPD and SSR markers. Genome 49:122-133.

Mehlenbacher S. A. and A. N. Miller. 1989. 'Barcelona' hazelnut. Fruit Var. J. 43:90-95.

Mehlenbacher, S. A., A. N. Azarenko, D. C. Smith, and R. McCluskey. 2007. 'Santiam' hazelnut. HortScience 42:715-717.

Mehlenbacher, S. A., D. C. Smith, and R. L. McCluskey. 2008. 'Sacajawea' hazelnut. HortScience 43:255 257.

Mehlenbacher, S. A., D. C. Smith, and R. L. McCluskey. 2009. 'Yamhill' hazelnut. HortScience 44:845-847.

Mehlenbacher, S. A., D. C. Smith, and R. L. McCluskey. 2011a. 'Jefferson' hazelnut. HortScience 46:662-664.

Mehlenbacher, S. A., D. C. Smith, R. L. McCluskey and M. M. Thompson. 2011b. 'Tonda Pacifica' hazelnut. HortScience 46:505-508.

Mehlenbacher, S. A., D. C. Smith, and R. L. McCluskey. 2013. 'Dorris' hazelnut. HortScience 48:796-799.

Mehlenbacher, S. A., D. C. Smith, and R. L. McCluskey. 2014. 'Wepster' hazelnut. HortScience 49:346-349.

Mehlenbacher, S. A., D. C. Smith, and R. L. McCluskey. 2016. 'McDonald' hazelnut. HortScience 51:757-760.

Molnar, T. J., J. C. Goffreda, and C. R. Funk. 2010a. Survey of *Corylus* resistance to *Anisogramma anomala* from different geographic regions. HortScience 45:832-836.

Molnar, T. J., J. M. Capik, S. Zhao, and N. Zhang. 2010b. First report of eastern filbert blight on *Corylus avellana* 'Gasaway' and 'VR20-11' caused by *Anisogramma anomala* in New Jersey. Plant Dis. 10:1265.

Molnar, T. J., S. A. Mehlenbacher, P. Engel, and J. M. Capik. 2019. Multiple sources of eastern filbert blight resistance provide breeding utility in New Jersey. J. Amer. Pomological Soc. 73: 178-192.

Muehlbauer, M. F., J. Tobia, J. A. Honig, N. Zhang, B. I. Hillman, K. Morey Gold, and T. J. Molnar. 2019. Population differentiation within *Anisogramma anomala* in North America. Phytopathology 109:1074-1082. https://doi.org/10.1094/PHYTO-06-18-0209-R.

Slate, G. L. 1952. Filbert varieties. Annu. Rep. Northern Nut Growers Assoc. 43:53-62.

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1 cacacgcctt gtcactcttt 20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2 ccccttttcac atgtttgctt 20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3 tggcagagct ttgtcagctt 20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4 gcagtggagg attgctgact 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5 cactcatacc gcaaactcca 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6 atggcttttg cttcgttttg 20

<210> SEQ ID NO 7
<211> LENGTH: 29

-continued

<212> TYPE: DNA
<213> ORGANISM: Artificial Sequence
<220> FEATURE:
<223> OTHER INFORMATION: Primer

<400> SEQUENCE: 7 tgcctctgca gttagtcatc aaatgtagg 29

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8 cgccatataa ttgggatgct tgttg 25

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9 tccgtgttga gtatggacga 20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10 tgtttttggt ggagcgatg 19

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11 agtcggctcc ccttttctc 19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12 gcgatctgac ctcatttttg 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13

-continued cctgcatcca ggactcatta 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14 gtgcagaggt tgcactcaaa 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15 gagagtgcgt cttcctctgg 20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16 agcctcacct ccaacgaac 19

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17 ttgccagtgc atactctgat g 21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18 accagctctg ggcttaacac 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19 ccaagcacga atgaactcaa 20

<210> SEQ ID NO 20
<211> LENGTH: 20

-continued

<212> TYPE: DNA
<213> ORGANISM: Artificial Sequence
<220> FEATURE:
<223> OTHER INFORMATION: Primer

<400> SEQUENCE: 20 gcgggttctc gttgtacact 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 caccctcttc accacctcat 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 catcccctgt tggagttttc 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23 ggctgacaac acagcagaaa 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24 tcggctaggg ttagggtttt 20

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25 aaactcaaat aaaacccctg ctc 23

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26

-continued aaactcaaat aaaacccctg ctc 23

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27 gttttgcgag ctcattgtca 20

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28 tgtgtgtggt ctgtaggcac t 21

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29 cattttccgc agataataca gg 22

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30 gtttccagat ctgcctccat ataat 25

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31 aagcaagaaa gggatggt 18

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32 cttacagata aatggctcaa a 21

<210> SEQ ID NO 33
<211> LENGTH: 21

-continued

<212> TYPE: DNA
<213> ORGANISM: Artificial Sequence
<220> FEATURE:
<223> OTHER INFORMATION: Primer

<400> SEQUENCE: 33 ggaaggtgag agaaatcaag t 21

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34 aggcatcagt tcatccaa 18

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35 gaacaactga agacagcaaa g 21

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36 aaggcggcac tcgctcac 18

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37 agaactccga ctaataatcc taacccttgc 30

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38 gagggagcaa gtcaaagttg agaagaaa 28

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39

-continued

```
tggaggaagt tttgaatggt agtagagga                                    29


<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40

aaagcaactc atagctgaag tccaatc                                      27
```

We claim:

1. A new and distinct variety of *Corylus* plant named 'OSU 541.147' as illustrated and described.

* * * * *

FIG. 6

Phenology Chart 1. Notes on female receptivity, pollen shed and leaf budbreak in Corvallis, OR (Dec. 2018- Mar. 2019).

| | Dec | | | | | Jan | | | | | | Feb | | | | | March | | | |
|---|---|---|---|---|---|---|---|---|---|---|---|---|---|---|---|---|---|---|---|---|
| Genotype | 5-Dec | 11-Dec | 18-Dec | 22-Dec | 30-Dec | 4-Jan | 6-Jan | 13-Jan | 20-Jan | 23-Jan | 30-Jan | 5-Feb | 10-Feb | 15-Feb | 19-Feb | 25-Feb | 3-Mar | 7-Mar | 11-Mar | 18-Mar |
| S41.147 | | | | | | | | | | 15 | 30 | 30 | 60 | 85 | 100-90 | 90 | done | | | BB 3/20 |
| (8 23) | | | | | | | | Rd | I+2/S | I+2/S+2 | I/S+3 | | I/S+3 | | S+3 | | gr tip | | | |
| | | | | | | | | | red | red | red | | | | blk | | | | | |
| McDonald | | | | | | | | 1 | 75 | 100 | 100-40 | 85 | done | | | gr tip | | | | BB 3/21 |
| (2 15) | | | | Rd- | | | Rd+2 | | Rd+2/I+ 2 | | Rd1+3 | I+2/S | | I+3/S | | | late flowers emerging | | I/S+2 | S+3 |
| | | | | | gr tip | | | | red | | | red | dark | dk-blk | | | | | red/dk-blk | |
| Wepster | | | | | | | | | 10 | 50 | 30 | 100-50 | 80 | done | | gr tip | | | | |
| (1 2) | | Rd+2 | | Rd+2 | | | Rd+2 | | | | Rd+2/I+2 | I+3 | I+3/S | I+2/S+2 | | | | | S+2 | BB 3/24 |
| | | | | | | | gr tip | | red | | | red | | dark | | | | | red/pk | |
| PollyO | | | | | | | | | | | 1 | 40 | 50 | 65 | 85 | 100 | 50 | 70 | 85 | BB 3/20 |
| (2 10) | | | Rd | | Rd+ | Rd+2 | | | Rd+2/I | I+2 | I+2/S | | | I+3/S | | | | | I/S+3 | |
| | | | | | | red | | | | | red | | | dark | | | | | black | |

Green = Pollen shed (a minus sign in front of the number indicates the percent of catkins that have already shed out).

Female flower stages: RD = Red dot; I = styles protruding ~1-3mm, straight; S = first appearance of 'spiders' or flowers with reflexed styles, and S+3 = majority of flowers are in 'spider' or fully reflexed stage.

Red = female flower color; red, blk (black), dk (dark, not quite red, not yet black).

FIG. 7

Phenology Chart 2. Notes on female receptivity, pollen shed, and leaf budbreak in East Brunswick, NJ (Dec. 2017 - Mar. 2018).

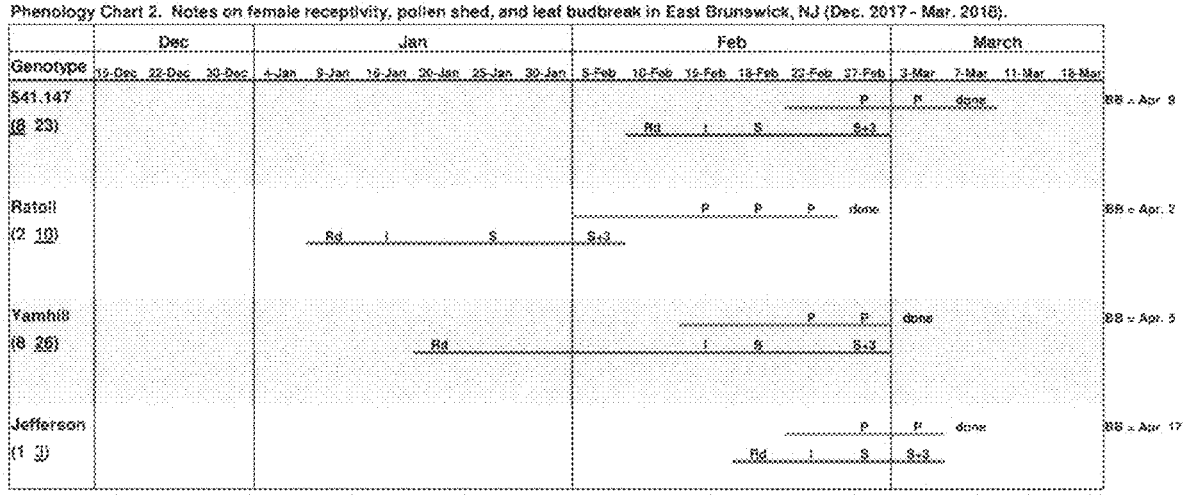

Red Bar - Flower stages: Rd= Red dot; I = styles protruding ~1-3 mm, straight, S = first appearance of 'spiders' or flowers with reflexed styles; S+3 = majority of flowers in 'spider' or fully reflexed stage.

Green Bar - Pollen stages: P signals actively shedding pollen. Green bar prior to P signals elongation stage.

BB = date of leaf budbreak

FIG. 8

Phenology Chart 3. Notes on female receptivity, pollen shed and leaf budbreak in East Brunswick, NJ (Dec. 2018- Mar. 2019).

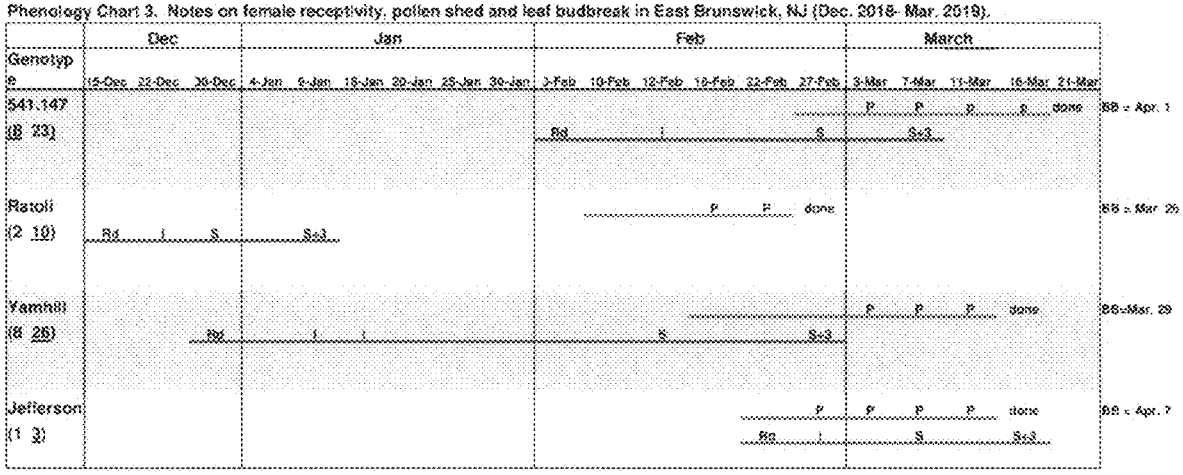

Red Bar - Flower stages: Rd= Red dot; i = styles protruding ~1-3 mm and straight; S = first appearance of 'spiders' or flowers with reflexed styles; S+3 = majority of flowers in 'spider' or fully reflexed stage.

Green Bar - Pollen stages: P signals actively shedding pollen. Green bar prior to P signals elongation stage.

BB = date of leaf budbreak